(12) United States Patent
Weitzner et al.

(10) Patent No.: US 9,011,320 B2
(45) Date of Patent: Apr. 21, 2015

(54) TRANSLUMINAL ENDOSCOPIC SURGERY KIT

(75) Inventors: Barry D. Weitzner, Acton, MA (US); William R. Roskopf, Pleasanton, CA (US); Russell F. Durgin, Bellingham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1495 days.

(21) Appl. No.: 12/287,151

(22) Filed: Oct. 6, 2008

(65) Prior Publication Data
US 2009/0143643 A1 Jun. 4, 2009

Related U.S. Application Data

(60) Provisional application No. 60/997,871, filed on Oct. 5, 2007.

(51) Int. Cl.
A61B 1/04 (2006.01)
A61B 17/34 (2006.01)
A61B 1/313 (2006.01)
A61B 1/00 (2006.01)
A61B 1/01 (2006.01)
A61B 19/00 (2006.01)
A61B 17/00 (2006.01)

(52) U.S. Cl.
CPC ......... *A61B 17/3423* (2013.01); *A61B 1/00135* (2013.01); *A61B 1/00142* (2013.01); *A61B 1/01* (2013.01); *A61B 1/313* (2013.01); *A61B 17/3478* (2013.01); *A61B 19/38* (2013.01); *A61B 2017/00278* (2013.01); *A61B 2017/3425* (2013.01); *A61B 2017/3488* (2013.01); *A61B 1/00087* (2013.01)

(58) Field of Classification Search
USPC ......... 600/104, 114, 121–123, 127, 129, 124, 600/125; 604/164.04, 164.07, 164.08; 606/144, 148
See application file for complete search history.

(56) References Cited

U.S. PATENT DOCUMENTS

| 3,254,651 | A | * | 6/1966 | Collito .......................... 606/153 |
| 4,624,255 | A | * | 11/1986 | Schenck et al. ............... 606/155 |
| 4,668,226 | A | | 5/1987 | Omata et al. |
| 4,946,442 | A | | 8/1990 | Sanagi |
| RE34,021 | E | | 8/1992 | Mueller et al. |
| 5,291,010 | A | * | 3/1994 | Tsuji .......................... 250/208.1 |
| 5,556,411 | A | * | 9/1996 | Taoda et al. ................... 606/185 |
| 5,746,694 | A | * | 5/1998 | Wilk et al. ..................... 600/123 |
| 5,785,689 | A | | 7/1998 | de Toledo et al. |

(Continued)

Primary Examiner — Anhtuan T Nguyen
Assistant Examiner — Timothy J Neal
(74) Attorney, Agent, or Firm — Bookoff McAndrews, PLLC

(57) ABSTRACT

A transluminal surgery kit and method of using the same. In one embodiment, the kit may include an endoscope, a surgical instrument, and an overtube. The surgical instrument may be an injection needle. The overtube, whose primary function is to provide a substantially sterile pathway for the surgical instrument, may include a tubular member having a proximal end, a distal end and a plurality of longitudinal bores. A film may cover the distal end of the tubular member. One of the bores may be appropriately dimensioned to coaxially receive the distal end of the endoscope, with the proximal end of the endoscope preferably not being inserted into the bore but extending proximally therefrom. A fastener for securing the tubular member to a lumen wall within a patient, together with a tool for inserting the fastener through the lumen wall, may be disposed within another one of the bores.

16 Claims, 25 Drawing Sheets

(56) References Cited

U.S. PATENT DOCUMENTS

| | | |
|---|---|---|
| 6,238,335 B1 | 5/2001 | Silverman et al. |
| 6,251,063 B1 | 6/2001 | Silverman et al. |
| 6,251,064 B1 | 6/2001 | Silverman et al. |
| 6,336,915 B1 | 1/2002 | Scarfone et al. |
| 6,401,718 B1 | 6/2002 | Johnson et al. |
| 6,423,034 B2 | 7/2002 | Scarfone et al. |
| 6,497,686 B1 | 12/2002 | Adams et al. |
| 6,524,234 B2 * | 2/2003 | Ouchi ............................ 600/127 |
| 6,585,694 B1 | 7/2003 | Smith et al. |
| 6,695,764 B2 * | 2/2004 | Silverman et al. ............... 600/29 |
| 6,770,053 B2 | 8/2004 | Scarfone et al. |
| 6,911,005 B2 * | 6/2005 | Ouchi et al. .................... 600/121 |
| 7,645,230 B2 * | 1/2010 | Mikkaichi et al. ............. 600/121 |
| 8,167,893 B2 * | 5/2012 | Motosugi ....................... 606/113 |
| 2005/0277945 A1 | 12/2005 | Saadat et al. |
| 2006/0258909 A1 | 11/2006 | Saadat et al. |

\* cited by examiner

TRANSLUMINAL ENDOSCOPIC SURGERY KIT

CROSS-REFERENCE TO RELATED APPLICATIONS

The present application claims the benefit under 35 U.S.C. 119(e) of U.S. Provisional Patent Application Ser. No. 60/997,871, filed Oct. 5, 2007, the disclosure of which is incorporated herein by reference.

BACKGROUND OF THE INVENTION

The present invention relates generally to endoscopes and relates more particularly to a transluminal endoscopic surgery kit.

Numerous medical procedures involve making an incision in body tissue and controlling any consequent bleeding. When performing these procedures, it is very important to minimize both tissue trauma during incision and the time required to stop internal bleeding. Minimally invasive procedures, such as those performed using endoscopy, are highly desirable because body tissue is usually traumatized less by these procedures than by more invasive conventional procedures.

In a typical endoscopic procedure, a patient is administered a mild sedative, and the distal end of an endoscope is inserted into the gastrointestinal tract through a natural orifice, such as the mouth or the anus, until the distal end of the endoscope is positioned near an area of interest within the GI tract. Next, an instrument suitable for use in performing a desired procedure on the area of interest is inserted into a working channel of the endoscope. An endoscopist then uses the instrument to perform the procedure on the area of interest. Once the procedure is complete, the instrument is withdrawn from the endoscope, and the endoscope is withdrawn from the patient.

An example of an endoscopic procedure of the type described above is disclosed in U.S. Pat. Nos. 6,238,335, 6,251,063, 6,251,064 and 6,695,764, all of which are incorporated herein by reference. More specifically, these patents disclose an endoscopic procedure for treating gastroesophageal reflux disease (GERD). GERD is a condition in which heartburn is severe enough or frequent enough to disrupt daily activities and/or sleep. Heartburn occurs when stomach fluids and acids escape from the stomach and enter into the esophagus, irritating the esophagus. Normally, a muscular ring called the lower esophageal sphincter (LES) acts as a valve between the esophagus and the stomach to allow food to pass from the esophagus into the stomach while keeping stomach fluids and acids from escaping from the stomach into the esophagus. In those instances in which the LES fails to keep stomach fluids and acids in the stomach, heartburn occurs. In some people who have GERD, the LES relaxes more than it should and/or at the wrong times. In addition to causing frequent and/or severe heartburn, GERD can cause other health problems. For example, the fluids and acids that reflux into the esophagus can lead to inflammation of the esophagus (esophagitis) or ulcers. In severe cases, this damage can scar the esophageal lining and narrow it, causing a stricture which may make it hard or painful for the patient to swallow. In certain cases, this may lead to a condition called Barrett's esophagus, where the lining of the esophagus changes and may over time lead to cancer of the esophagus.

The endoscopic procedure described in the above patents involves inserting an endoscope down through the patient's mouth and into the esophagus in proximity to the LES. Then, the distal end of a device commonly referred to as "an injection needle" is inserted through a working channel of the endoscope until a needle at the distal end of the injection needle is inserted into the muscle of the LES. Then, a special solution is dispensed through the injection needle and into the muscle of the LES. The solution includes a biocompatible polymer that forms a soft, spongy, permanent implant in the sphincter muscle that helps the LES to keep stomach fluids and acids from backing up into the esophagus.

Typically, an injection needle of the type referred to above comprises a hollow needle, a flexible inner catheter, a flexible outer catheter, an inner hub and an outer hub. The proximal end of the hollow needle is typically fixedly mounted within the distal end of the flexible inner catheter. The inner hub is typically fixedly mounted on the proximal end of the inner catheter and is adapted to convey fluids to the inner catheter from a needleless syringe or the like. The inner catheter and the hollow needle are typically slidably mounted within the outer catheter so that one may extend the hollow needle out of the distal end of the outer catheter when one wishes to make an injection and retract the hollow needle into the outer catheter when not making an injection. The outer hub is typically fixedly mounted on the proximal end of the outer catheter and is adapted to engage the inner hub so as to limit the distal movement of the needle and the inner catheter relative to the outer catheter. Examples of injection needles are disclosed in the following patents, all of which are incorporated herein by reference: U.S. Pat. Nos. 6,770,053; 6,585,694; 6,423,034; 6,401,718; 6,336,915; 5,785,689; 4,946,442; and 4,668,226.

A newly emerging area of medicine is NOTES, i.e., Natural Orifice Transluminal Endoscopic Surgery. In NOTES, endoscopic procedures are performed in the abdominal cavity using an endoscope that has been inserted through a natural orifice and is then passed through an incision in the gastrointestinal tract and into the abdominal cavity. More specifically, the NOTES procedure typically involves inserting the distal end of an endoscope through a natural orifice, such as the mouth or anus, and into the gastrointestinal tract, creating an opening at a desired location within the gastrointestinal tract (e.g., the stomach, the esophagus, the large intestine, the small intestine), dilating the opening, and passing the endoscope through the dilated opening into the abdominal cavity. The distal end of the endoscope may then be advanced to a target area within the cavity, and a surgical procedure may then be performed on the target area using instruments delivered by the endoscope. Examples of procedures for which NOTES may be suitable include appendectomies and cholecystectomies. Other natural orifices for which NOTES may be suitable include the vagina and the urethra.

SUMMARY OF THE INVENTION

According to one aspect of the invention, there is provided a transluminal endoscopic surgery kit, said transluminal endoscopic surgical kit comprising (a) an access tube, the access tube comprising a proximal end, a distal end, and a channel; (b) a surgical instrument, the surgical instrument being adapted for removable insertion into the channel of the access tube; and (c) an overtube, the overtube having a proximal end, a distal end and a longitudinally-extending bore, the longitudinally-extending bore being adapted to removably receive the distal end of the access tube, the distal end of the overtube being adapted to be secured to a lumen wall within a patient.

According to another aspect of the invention, there is provided an injection needle, said injection needle comprising (a) an inner catheter, said inner catheter having a proximal end, a distal end, and a longitudinal bore; (b) a hollow needle, said hollow needle having a proximal end and a distal end, said proximal end of said hollow needle being coaxially mounted within said distal end of said inner catheter, said hollow needle having an outer diameter of at least that of a 9 gauge needle; and (c) an outer catheter, said outer catheter having a proximal end, a distal end, and a longitudinal bore, said inner catheter and said hollow needle being coaxially mounted within said outer catheter and being movable between an extended position in which said hollow needle extends distally beyond said distal end of said outer catheter and a retracted position in which said hollow needle does not extend distally beyond said distal end of said outer catheter.

According to still another aspect of the invention, there is provided an overtube for an access tube, said overtube comprising a proximal end, a distal end and a longitudinally-extending bore, said longitudinally-extending bore being adapted to removably receive a distal end of an access tube, said distal end of said overtube being adapted to be secured to a lumen wall within a patient.

According to still yet another aspect of the invention, there is provided an overtube for an access tube, the overtube comprising a tubular member having a proximal end, a distal end and a plurality of bores, one of the plurality of bores being adapted to removably receive a distal end of an access tube, the overtube further comprising a fastener disposed in another one of the plurality of bores.

According to even still yet another aspect of the invention, there is provided a method of accessing a body organ with a needle, the method comprising the steps of (a) providing an overtube, the overtube having a proximal end, a distal end and a longitudinally-extending bore, the longitudinally-extending bore being adapted to removably receive a distal end of an access tube, the distal end of the overtube being adapted to be secured to a lumen wall within a patient; (b) inserting the distal end of the overtube into a lumen within a patient while keeping the proximal end of the overtube external to the patient; (c) securing the distal end of the overtube to a wall of the lumen while keeping the proximal end of the overtube external to the patient; (d) inserting a distal end of an access tube into the overtube; (e) forming a perforation in the wall of the lumen using a perforating tool inserted into the access tube; (f) inserting a distal end of a needle into the access tube; and (g) passing the distal end of the needle through the perforation in the wall of the lumen.

According to a further aspect of the invention, there is provided a method of performing a transluminal surgery, said method comprising the steps of (a) providing an overtube, said overtube having a proximal end, a distal end and a longitudinally-extending bore, said longitudinally-extending bore being adapted to removably receive a distal end of an endoscope, said distal end of said overtube being adapted to be secured to a lumen wall within a patient; (b) inserting said distal end of said overtube into a lumen within a patient while keeping said proximal end of said overtube external to the patient; (c) securing said distal end of said overtube to a wall of said lumen while keeping said proximal end of said overtube external to the patient; (d) forming a perforation in the wall of the lumen using a perforating tool inserted into said overtube; (e) inserting a distal end of an endoscope into said overtube; (f) inserting a distal end of a surgical instrument into said endoscope; (g) passing the distal end of said surgical instrument through the perforation in the wall of the lumen; (h) performing a surgical procedure on a target accessed through the perforation using said surgical instrument.

For purposes of the present specification and claims, various relational terms like "top," "bottom," "proximal," "distal," "upper," "lower," "front," and "rear" are used to describe the present invention when said invention is positioned in or viewed from a given orientation. It is to be understood that, by altering the orientation of the invention, certain relational terms may need to be adjusted accordingly.

Various objects, features and advantages of the present invention will be set forth in part in the description which follows, and in part will be obvious from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention: In the drawings wherein like reference numerals represent like parts.

DETAILED DESCRIPTION OF PREFERRED EMBODIMENTS

Figure 1:
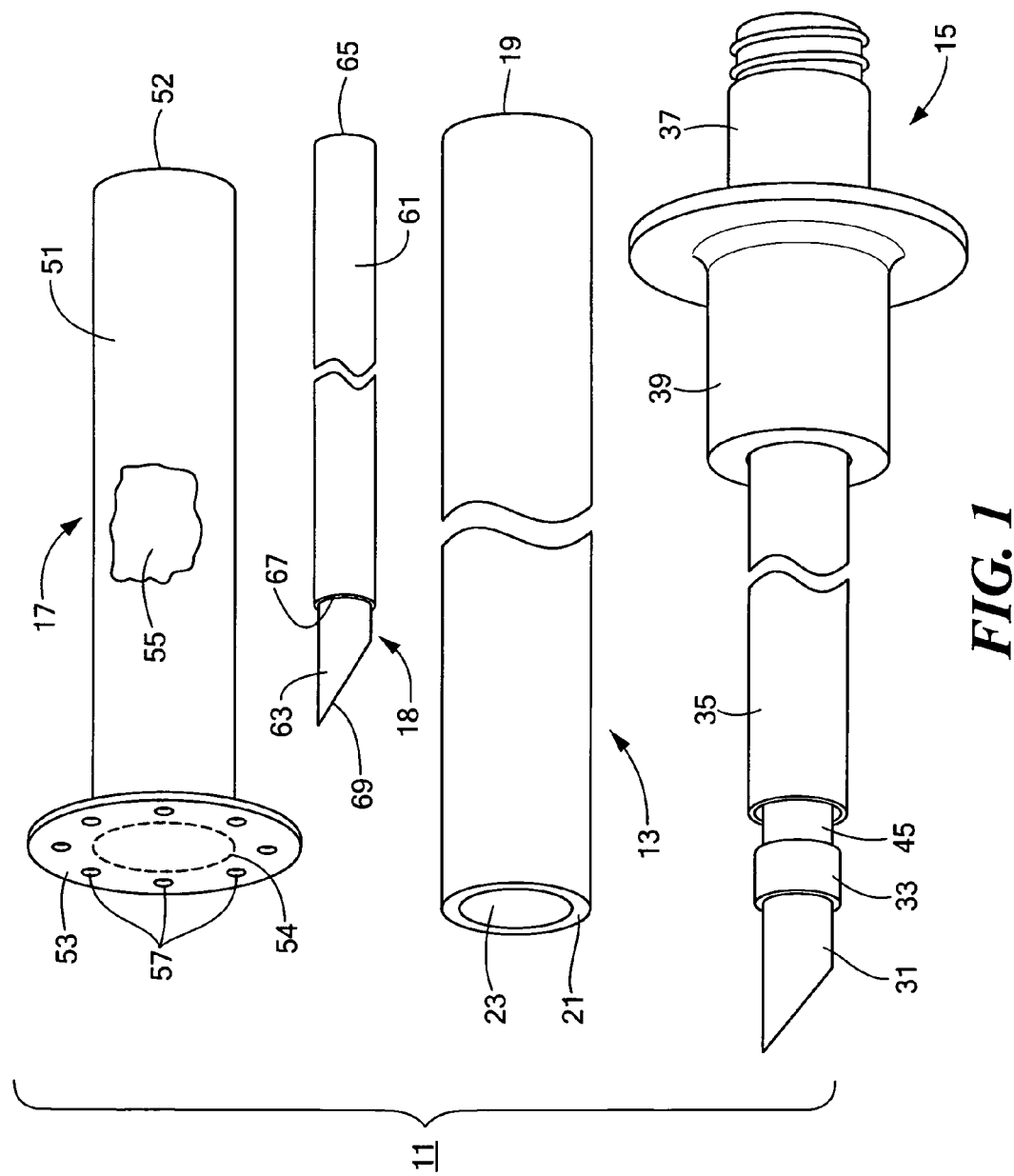
FIG. 1 is a perspective view, broken away in part, of a first embodiment of a transluminal surgery kit constructed according to the teachings of the present invention, the transluminal surgery kit being shown in an unassembled state with the needle of the injection needle being shown in a fully extended position.

Referring now to FIG. 1, there is shown a perspective view, broken away in part, of a first embodiment of a transluminal surgery kit constructed according to the teachings of the present invention, said transluminal surgery kit being shown prior to use and preferably in a sterile state and being represented generally by reference numeral 11.

Kit 11, which may be used, for example, in transgastric injections, transesophageal injections, or transintestinal injections, may comprise an endoscope 13, an injection needle 15, an overtube 17, and a perforating tool 18.

Endoscope 13, which may be similar in many respects to conventional endoscopes, may be an elongated, flexible member having a proximal end 19, a distal end 21, and a longitudinal bore or working channel 23. In some embodiments, working channel 23 may have a diameter of about 6 mm, and endoscope 13 may have an outer diameter of about 10 mm.

Figure 2:
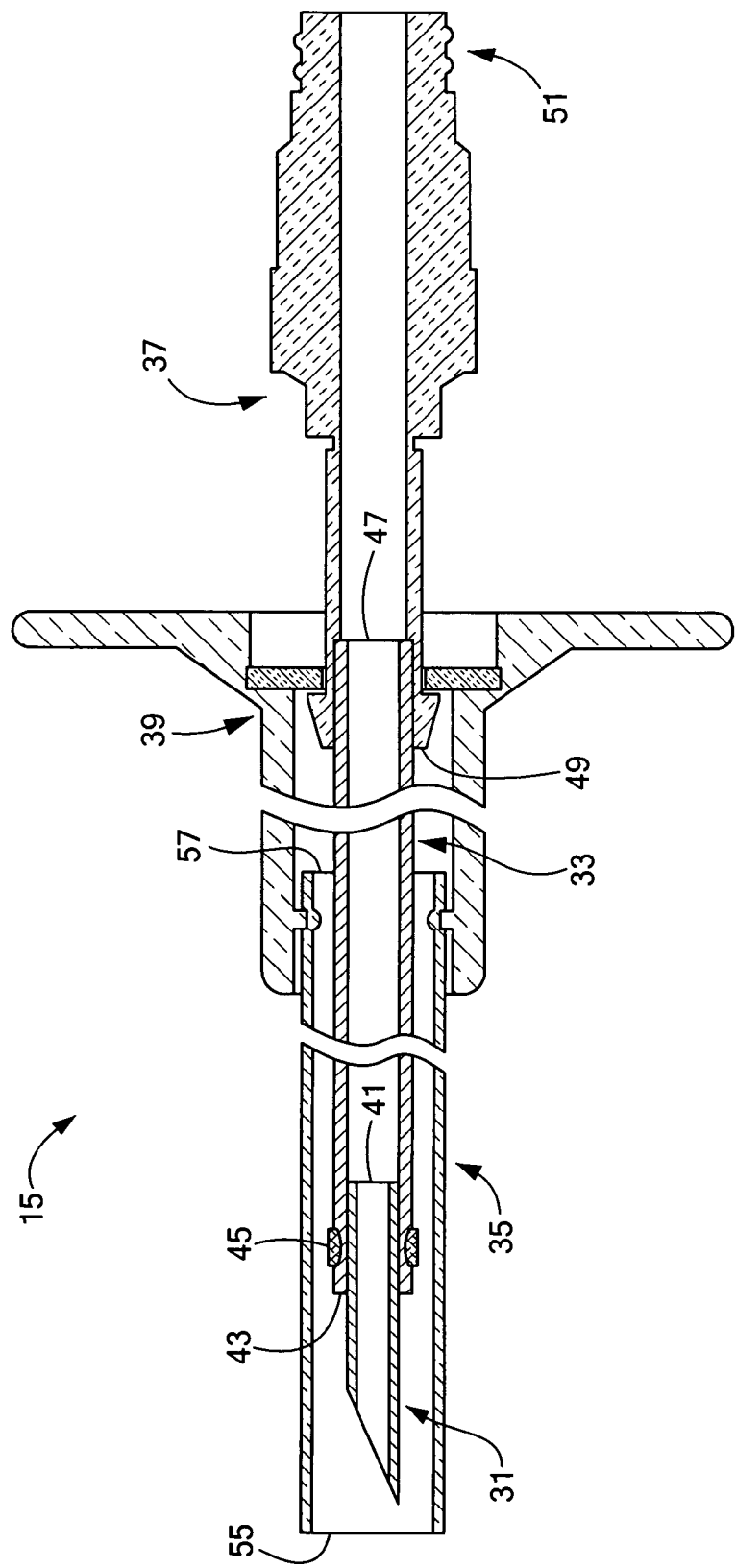
FIG. 2 is a longitudinal section view of the injection needle shown in FIG. 1, with the needle being shown in a fully retracted position.

Injection needle 15, which is also shown separately in FIG. 2 with its needle in a fully retracted position, may be similar in many respects to conventional injection needles. Injection needle 15 may comprise a hollow needle 31, a flexible inner catheter (or a stainless steel or nitinol (a nickel/titanium alloy) hypotube) 33, a flexible outer catheter 35, a tubular inner hub 37 and a tubular outer hub 39. The proximal end 41 of hollow needle 31 may be fixedly mounted within the distal end 43 of flexible inner catheter 33 by a metal band 45 that may be crimped around the outside of inner catheter 33. The proximal end 47 of inner catheter 33 may be fixedly mounted within the distal end 49 of inner hub 37. The proximal end 51 of inner hub 37 may be externally threaded and may be adapted for connection to a conventional needleless syringe or the like. Inner catheter 33 and hollow needle 31 may be slidably mounted within outer catheter 35 so that one may extend hollow needle 31 out of the distal end 55 of outer catheter 35 when one wishes to make an injection and so that one may retract hollow needle 31 into outer catheter 35 when not making an injection. Outer hub 39 may be fixedly mounted over the proximal end 57 of outer catheter 35 and may be adapted to engage inner hub 37 so as to limit the distal movement of needle 31 and inner catheter 33 relative to outer catheter 35.

Injection needle 15 may be removably mounted in endoscope 13, with the distal end of injection needle 15 (e.g., needle 31, distal end 43 of inner catheter 33, distal end 55 of outer catheter 35) being inserted into working channel 23 of endoscope 13 and with inner hub 37 and outer hub 39 preferably not being inserted into working channel 23. If desired, needle 31, inner catheter 33 and outer catheter 35 may be as large in diameter as can be accommodated by working channel 23. Accordingly, where, as in the present embodiment, working channel 23 has a diameter of approximately 4-8 mm, needle 31 may be at least as large as a 9 gauge needle (i.e., outer diameter of approximately 0.15 inch). Notwithstanding the above, if desired, needle 31, inner catheter 33 and outer catheter 35 may be appropriately dimensioned to permit fiber optics or other direct visualization means to also be inserted into working channel 23.

Overtube 17, whose primary function is to provide a substantially sterile environment for accessing the peritoneal cavity, may comprise a proximal portion 51 and a distal portion 53. Proximal portion 51 may be an elongated tubular member having a proximal end 52, a distal end 54 and a longitudinal bore 55. Bore 55 may be appropriately dimensioned to coaxially receive distal end 21 of endoscope 13, with proximal end 19 of endoscope 13 preferably not being inserted into bore 55 but extending proximally therefrom. (Although proximal portion 51 is shown in the present embodiment as having a cylindrical shape, proximal portion 51 is not limited to such a shape and may have any geometry, for example, oval.) Distal portion 53, which may be generally disc-shaped, may be positioned over distal end 54 of proximal portion 51 and may extend radially outwardly to define an external flange. (Preferably, distal portion 53 has an outer diameter no greater than about 20 mm to permit its passage through the esophagus.) A plurality of transverse openings 57 may be evenly spaced on distal portion 53 at positions located radially outwardly of proximal portion 51. As will be discussed further below, openings 57 may be dimensioned to receive fasteners. (Alternatively, openings 57 may be omitted, and fasteners may be inserted directly through the external flange portion of distal portion 53.)

Overtube 17 may be made of a preferably flexible, biocompatible material and may be a unitary structure made of a silicone rubber, a thermoplastic elastomer, a braided catheter, or a similar material. Alternatively, instead of being a unitary structure, proximal portion 51 and distal portion 53 may be fabricated separately and then joined together, or distal portion 53 may be overmolded around proximal portion 51 or vice versa.

Perforating tool 18, which may be a conventional perforating tool, may comprise a flexible tube 61 and a piercing element 63. Tube 61, which may be made of a silicone rubber or the like, may be an elongated, unitary member having a proximal end 65 and a distal end 67. Tip 63, which may be a solid, metal member having a sharpened distal end 69, may be fixedly mounted within distal end 67 of tube 61.

Figure 3A:
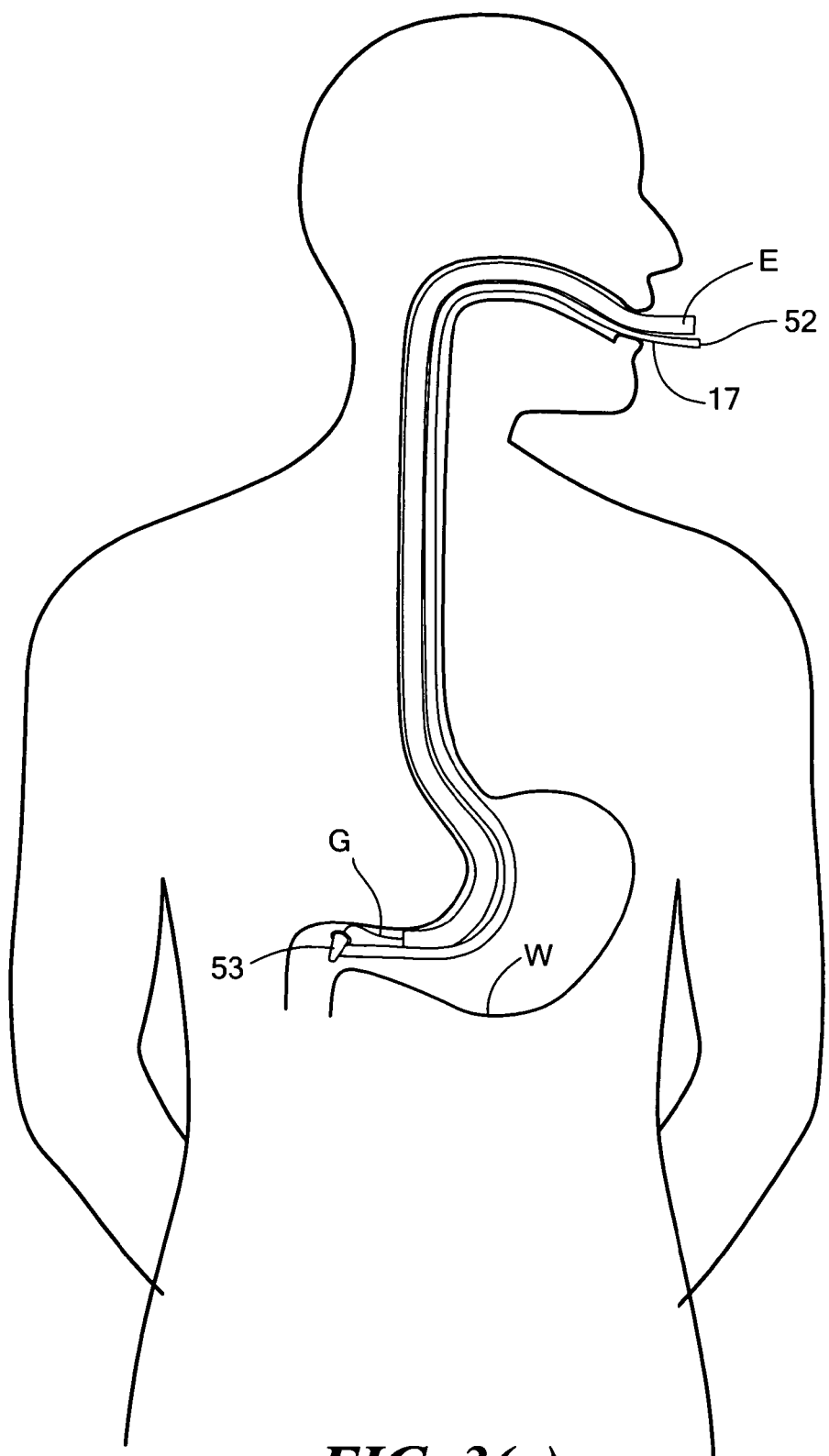
FIGS. 3(a) through 3(f) are fragmentary schematic views, partly in section, illustrating one way in which the transluminal surgery kit of FIG. 1 may be used in accordance with the teachings of the present invention.
Figure 3B:
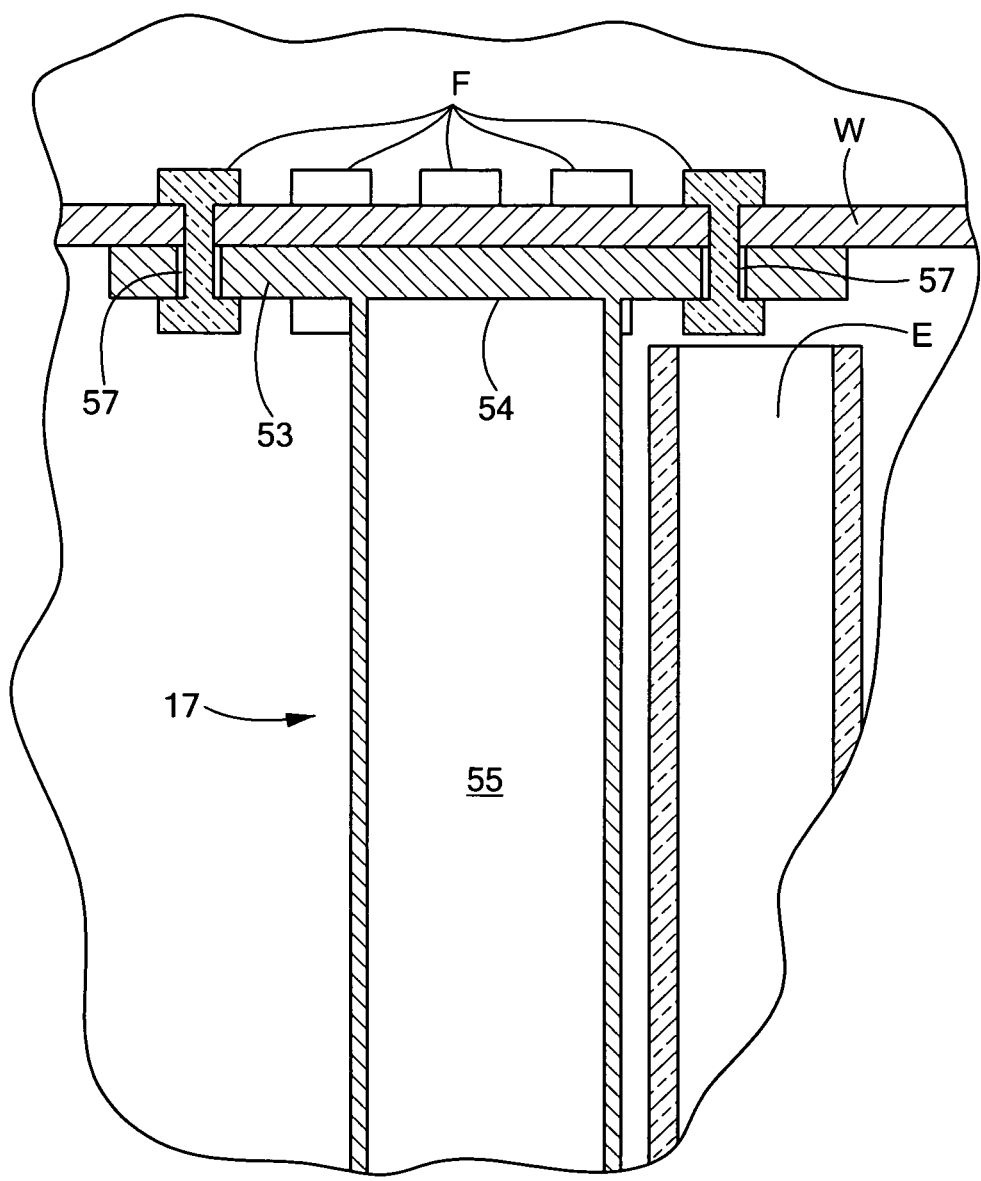
Figure 3C:
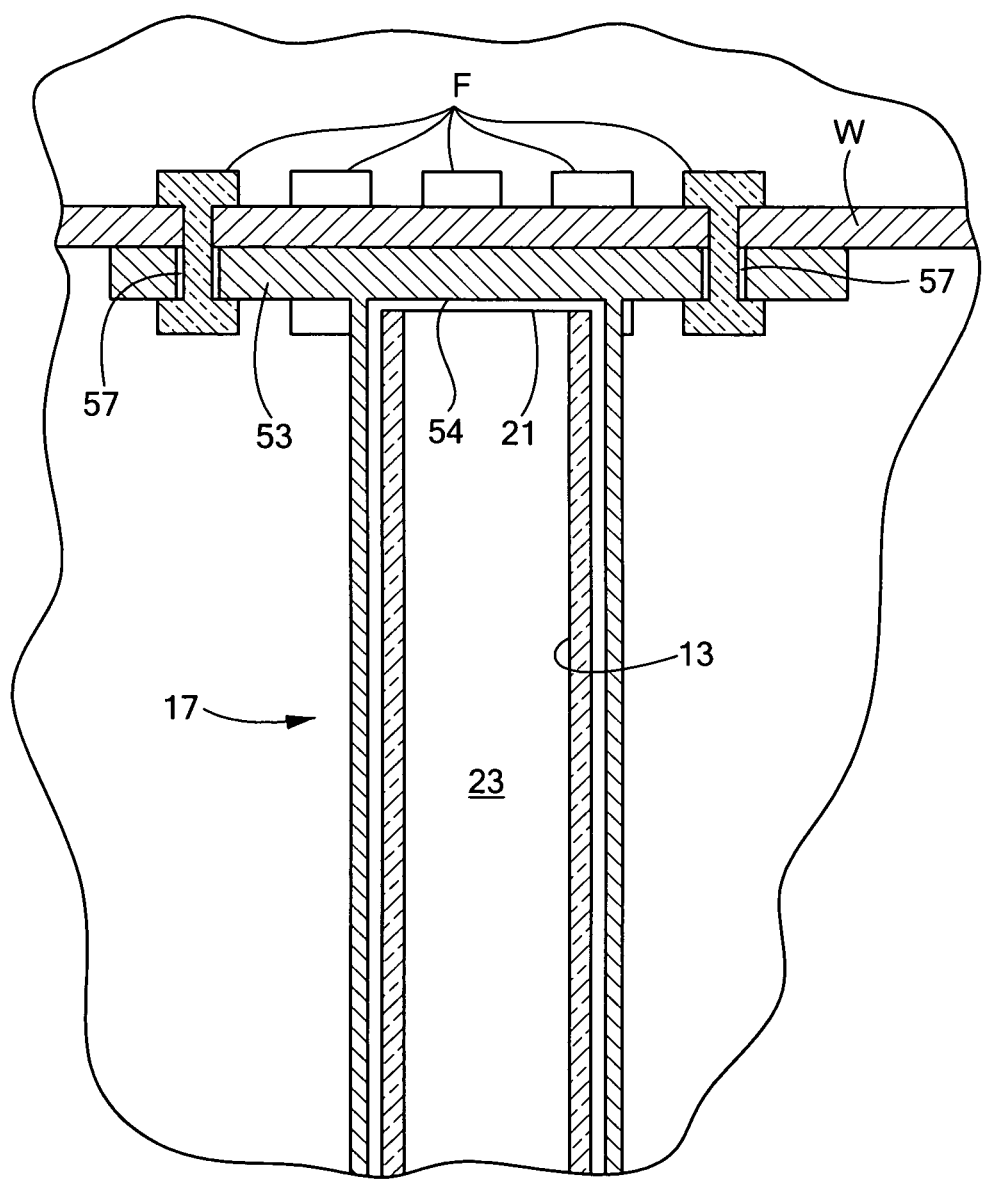
Figure 3D:
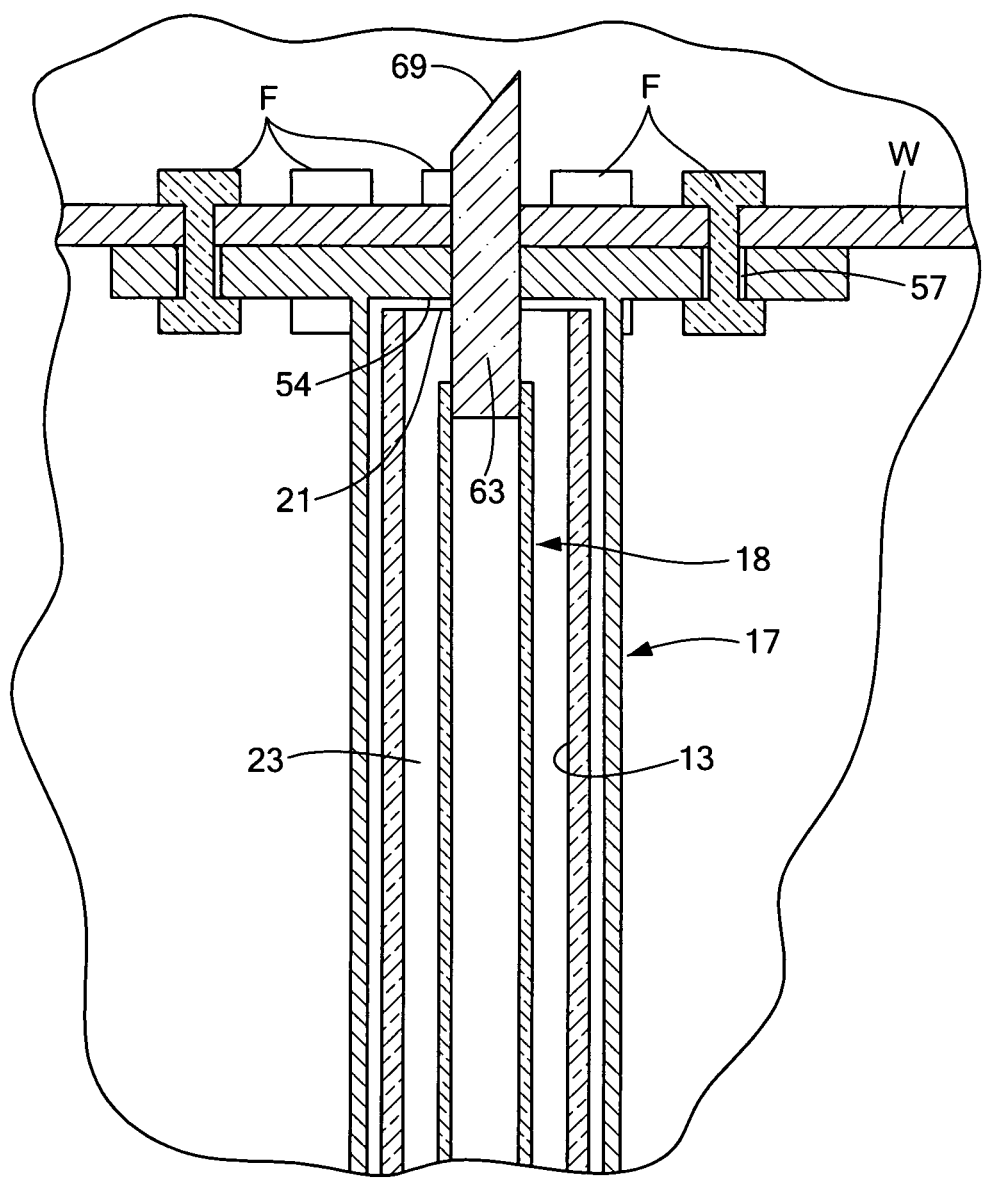
Figure 3E:
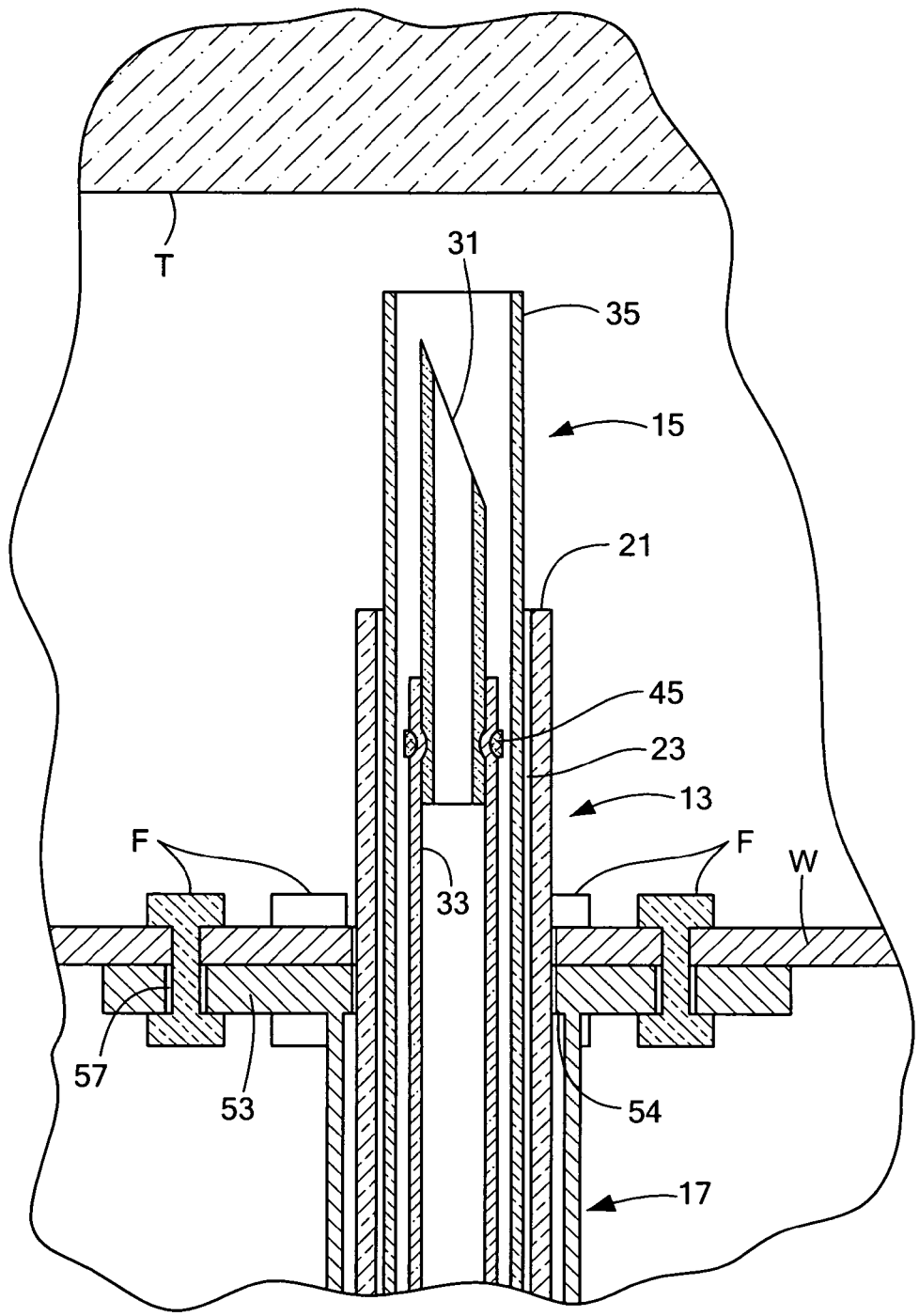
Figure 3F:
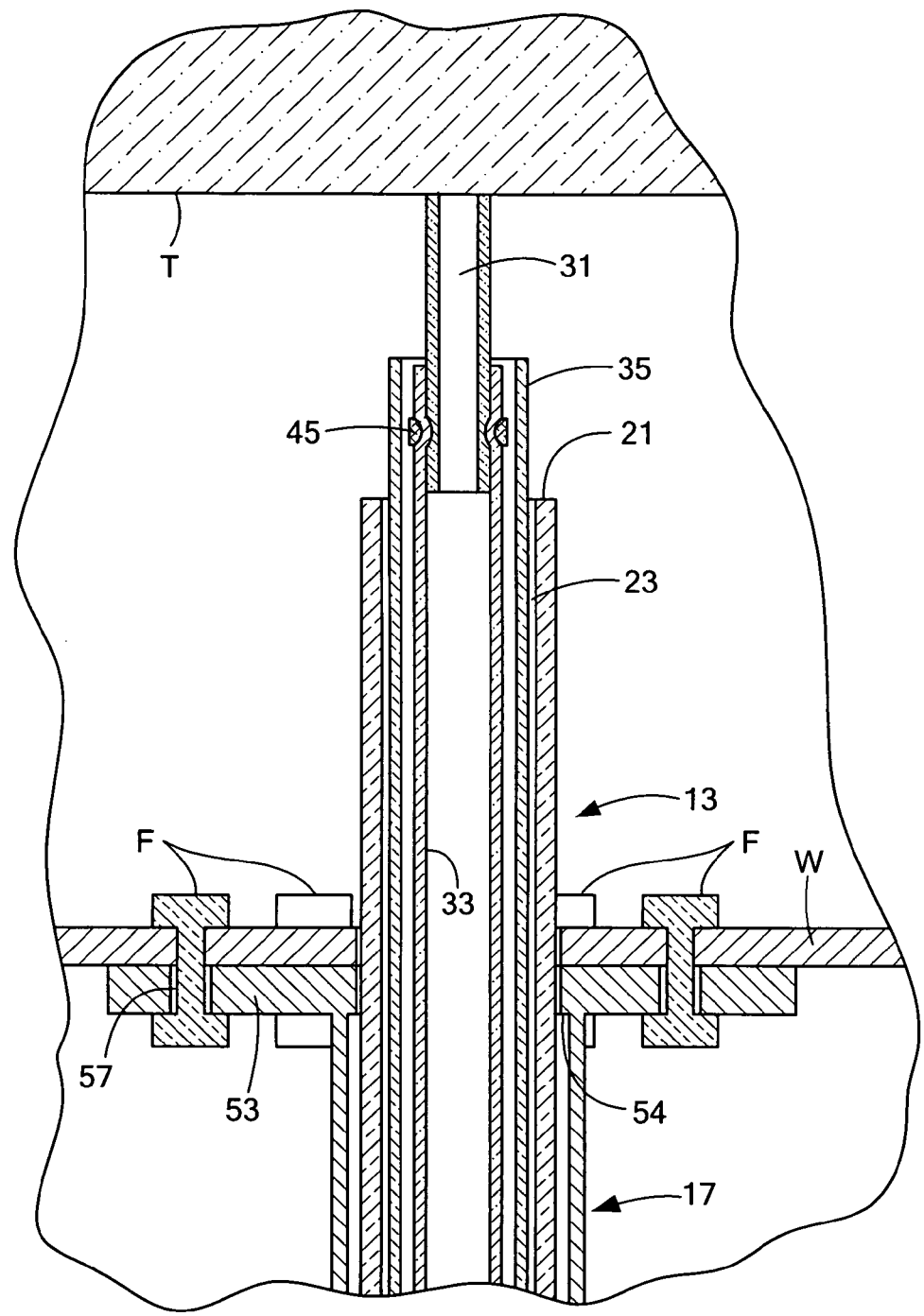

Referring now to FIGS. 3(a) through 3(f), there are shown various views that schematically illustrate one way in which transluminal surgery kit 11 may be used. (In these views, kit 11 is being used to perform a transgastric injection; however, it should be understood that kit 11 could alternatively be used to perform, for example, a transesophageal injection, a transintestinal injection, or any other procedure that operates through a natural orifice or lumen in the body.) First, as seen in FIG. 3(a), using a conventional endoscope E that is equipped with a grasping instrument G (such as a forceps), one grasps distal portion 53 of a sterile overtube 17 with grasping instrument G and then inserts both the distal end of endoscope E and distal portion 53 of overtube 17 through the mouth of a patient and into the stomach of the patient until distal portion 53 is positioned at a desired location within the stomach of the patient. As can be seen, for example, when delivering distal portion 53 to the stomach of the patient, proximal end 52 of overtube 17 is not inserted at all into the patient. In this manner, the sterility of the interior of overtube 17 may be maintained even as the distal end of overtube 17 is drawn through the mouth of the patient (the mouth being a non-sterile environment) since the interior of overtube 17 is not exposed to the mouth of the patient. Moreover, because endoscope E does not come into contact with any part of the interior of overtube 17, the sterility of the interior of overtube 17 is unaffected by endoscope E, which itself may be non-sterile. Next, as seen in FIG. 3(b), one then removes grasping instrument G from the working channel of delivery endoscope E and uses the working channel of endoscope E to insert fasteners F (e.g., staples, T-fasteners, clips, etc.) across openings 57 and across the stomach wall W of the patient, thereby securing overtube 17 to the stomach wall W. (Alternatively, the fasteners may be coupled to overtube 17 prior to insertion of overtube 17 into the patient, and fastening could occur by pushing overtube 17 against the tissue or by actuating a trigger mechanism to deploy fasteners.) Preferably, distal portion 53 remains in close contact with the stomach (or other organ) to maintain sterility and to prevent leakage or bleeding. Next, as seen in FIG. 3(c), one then removes endoscope E from the patient and inserts a sterile endoscope 13 into overtube 17 until distal end 21 of endoscope 13 is positioned in the vicinity of distal portion 53 of overtube 17. Next, as seen in FIG. 3(d), one inserts a sterile perforating tool 18 into working channel 23 of endoscope 13 and then uses perforating tool 18 to perforate distal portion 53 of overtube 17 and stomach wall W. Next, as seen in FIG. 3(e), one removes perforating tool 18 from endoscope 13 and then inserts the distal end of a sterile injection needle 15 (with needle 31 in a fully retracted position) into working channel 23 of endoscope 13 and through the perforations in overtube 17 and stomach wall W until the distal end of injection needle 15 is positioned near a target tissue T in the peritoneal cavity. Next, as seen in FIG. 3(f), one moves needle 31 of injection needle 15 to its extended position and then inserts needle 31 into the target tissue T. Materials may then be dispensed into target tissue T through injection needle 15 in a conventional manner. (Alternatively, instead of using injection needle 15 to dispense materials into tissue T, injection needle 15 may be used to aspirate fluids or even to remove tissue.) It should be noted that, because needle 31 may be larger in inner diameter than the needles of conventional injection needles, needle 31 may be better suited for dispensing large volumes of materials, as well as higher viscosity materials and materials including particulate matter, such as radioactive beads, drug delivery matrices, bulking beads and agents, sponges, etc. After the injection of materials into target tissue T is complete, one may move needle 31 back to its fully retracted position and then removes injection needle 15 and endoscope 13 from the patient. Thereafter, fasteners F are removed, and overtube 17 is removed from the patient.

As can be appreciated, one benefit of using overtube 17 is that fluids, blood, food, fecal matter, urine, toxins, etc. are prevented from escaping the organ or lumen.

One application of the present invention is in the site-specific delivery of chemotherapeutic agents.

It should be understood that, although the above-described method involves a transoral introduction of kit 11 into a patient, a transanal approach may alternatively be used. One factor that may be considered in determining whether to utilize a transoral approach or a transanal approach is the location of the target structure in the patient and, hence, the optimal location for entering the abdominal cavity from the gastrointestinal tract. Another factor that may be considered is that a transanal approach may have a higher need for a sterile environment during surgery.

Figure 4:
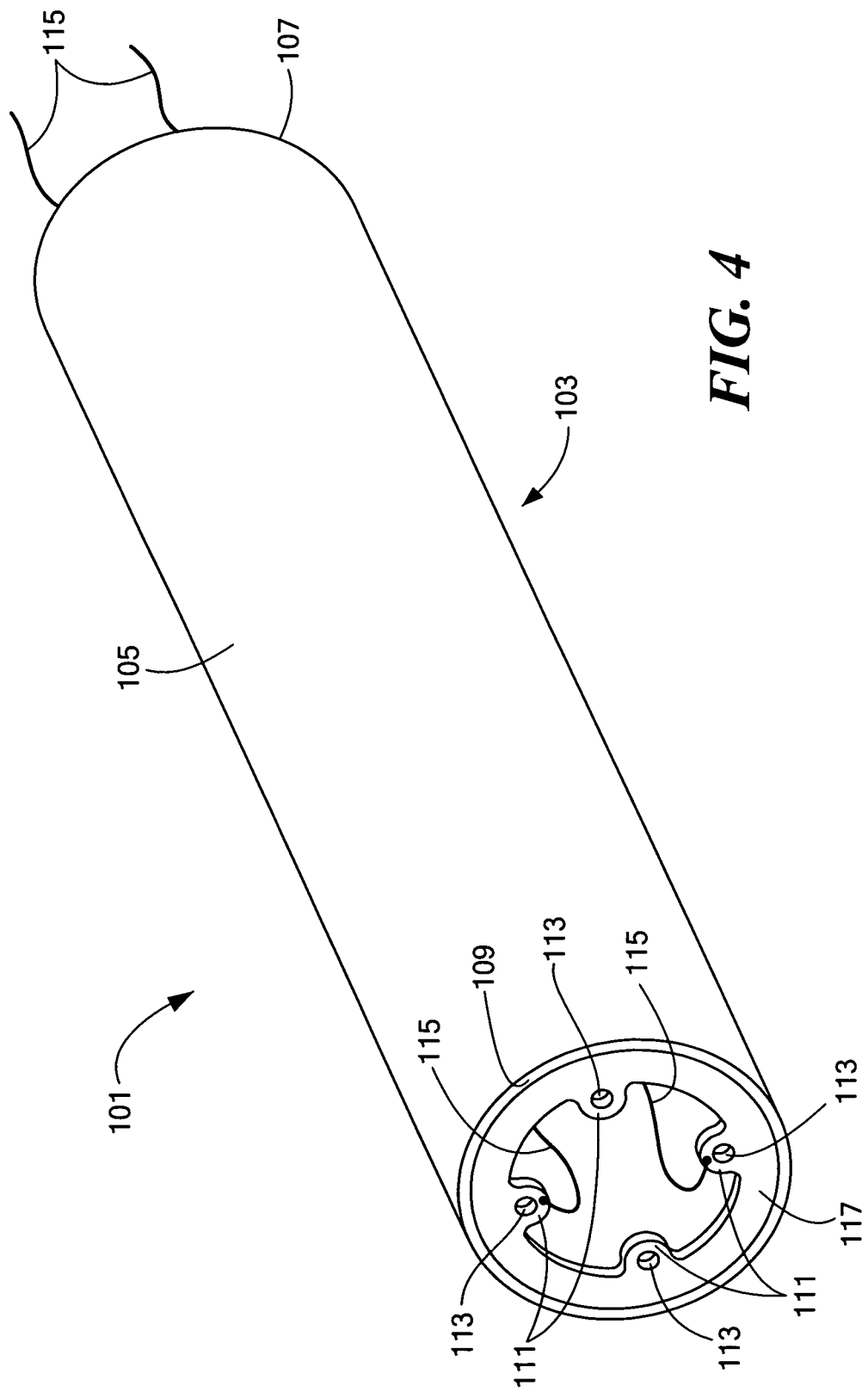
FIG. 4 is a perspective view of a first alternate overtube for use in the transluminal surgery kit of FIG. 1.

Referring now to FIG. 4, there is shown a perspective view of a first alternate embodiment of an overtube adapted for use with kit 11, said overtube being represented generally by reference numeral 101.

Overtube 101 may comprise an elongated, tubular member 103. Tubular member 103 may be a unitary structure made of a flexible material, such as a silicone rubber, a thermoplastic elastomer or a similar material. Tubular member 103 may be shaped to include a side wall 105, an open proximal end 107, a generally annular distal end 109, and a longitudinal bore 110. (Although side wall 105 is shown in the present embodiment as having a cylindrical shape, side wall 105 is not limited to such a shape and may have any geometry, for example, oval.) Distal end 109 may be shaped to include a plurality of tabs 111, tabs 111 extending radially inwardly a short distance. A transverse opening 113 may be provided in each of tabs 111, each opening 113 being adapted to receive a fastener, such as a surgical staple, a suture or the like. In addition, a string 115 may be secured to each of two tabs 111 that are diametrically-opposed to one another, strings 115 being adapted to be drawn proximally through bore 110 and to extend proximally beyond proximal end 107 by a distance to become apparent below.

Overtube 101 may further comprise a thin film 117, film 117 sealably covering the central opening provided in distal end 109 of tubular member 103. Film 117, as well as any other part or the entirety of overtube 101, may be optically clear so that the proper placement of distal end 109 at a desired location within the GI tract may be ensured using visualization means provided in an endoscope positioned within overtube 101.

Figure 5A:
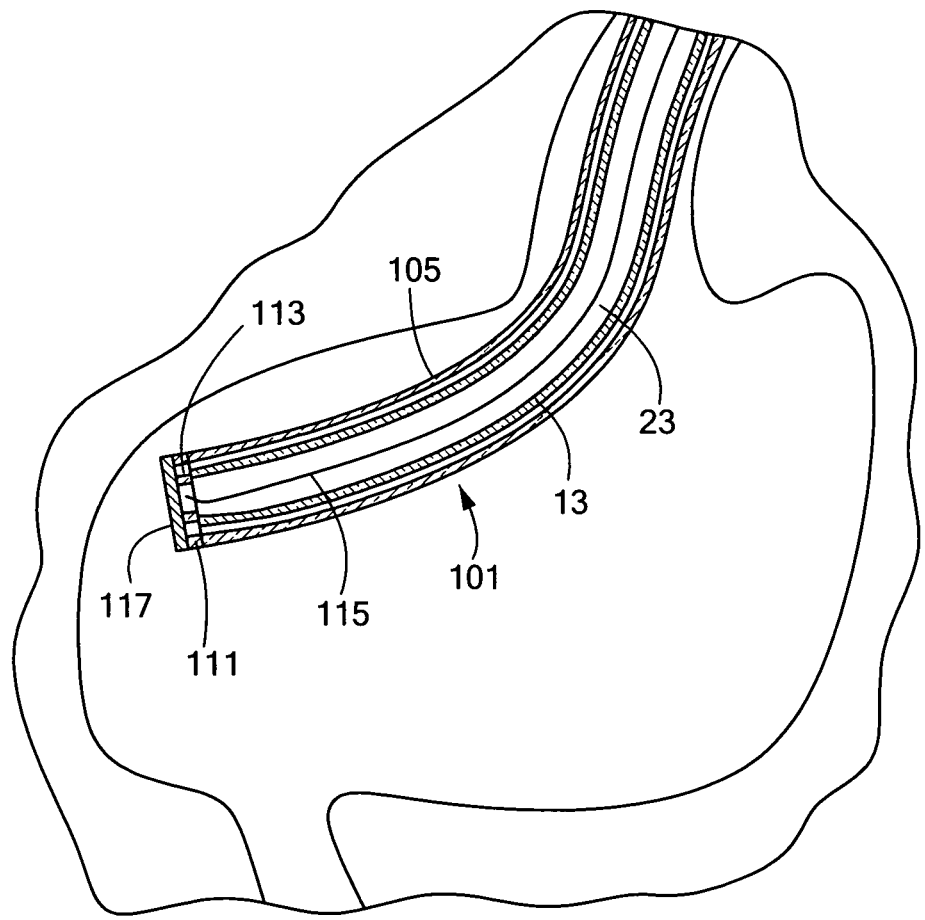
FIGS. 5(a) through 5(e) are fragmentary schematic views, partly in section, illustrating one way in which the overtube of FIG. 4 may be used in accordance with the teachings of the present invention.
Figure 5B:
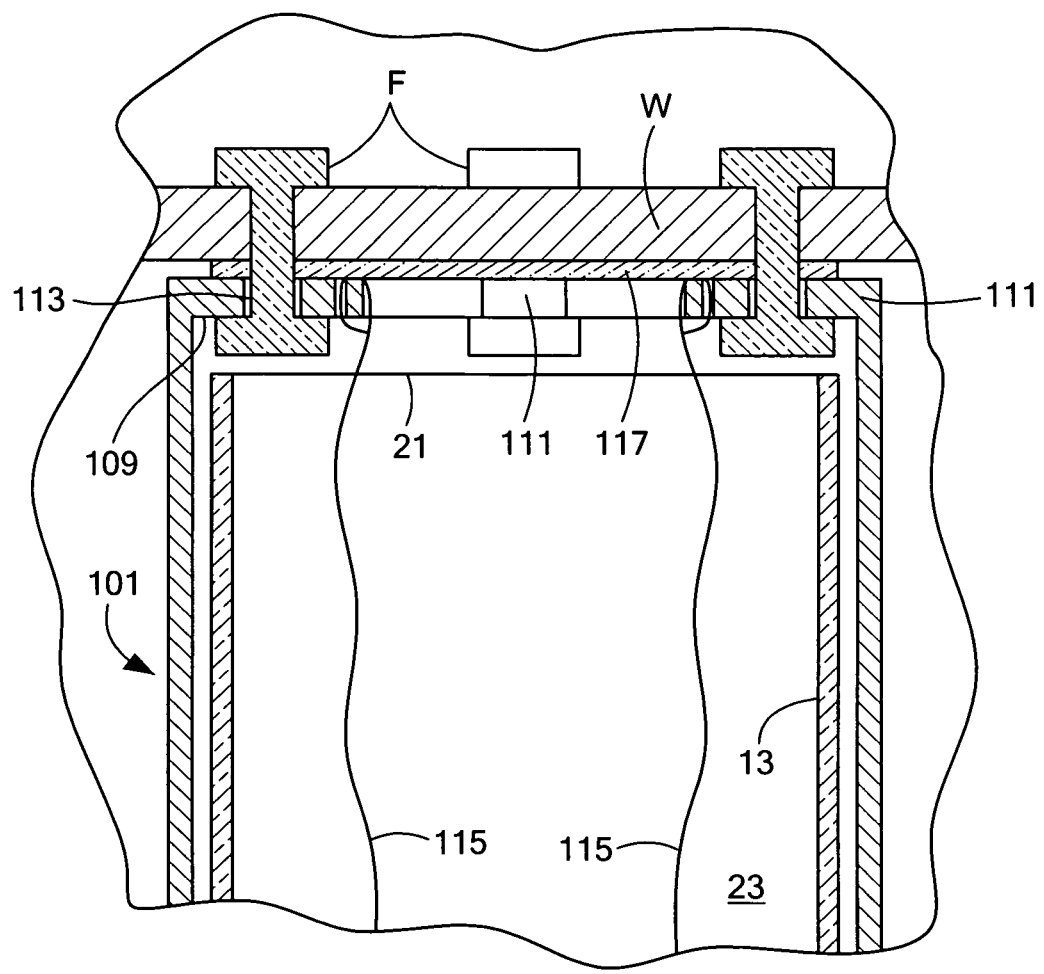
Figure 5C:
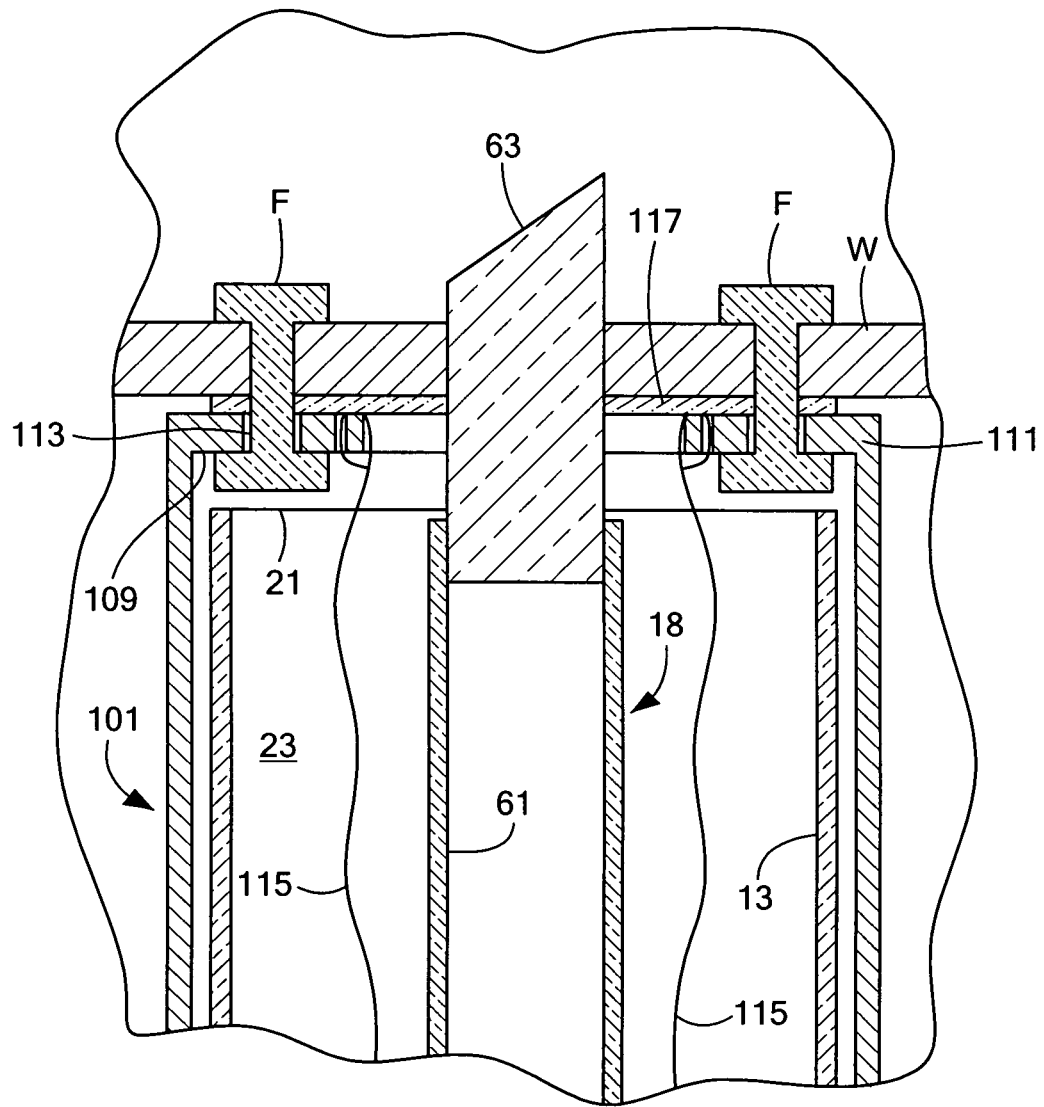
Figure 5D:
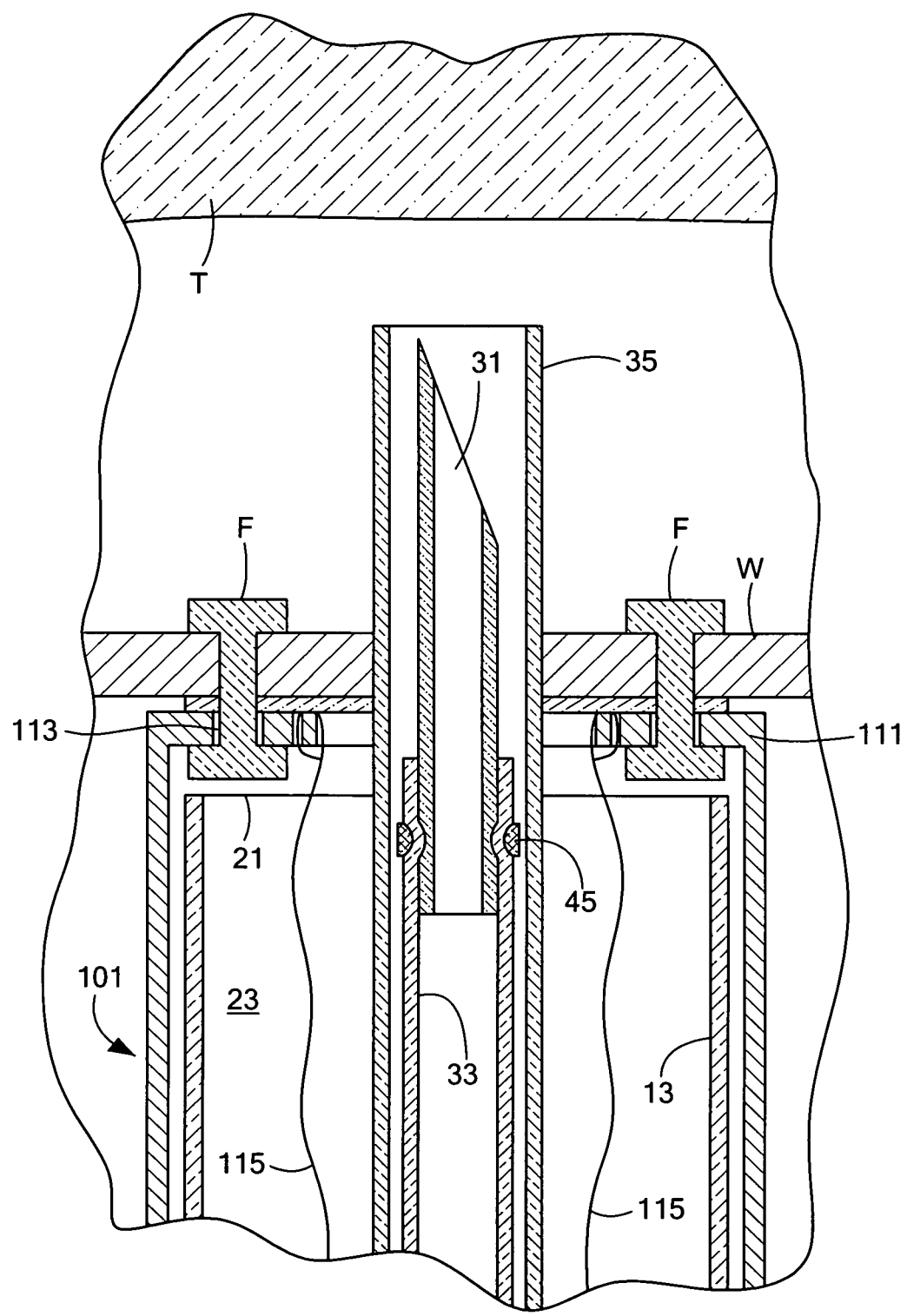
Figure 5E:
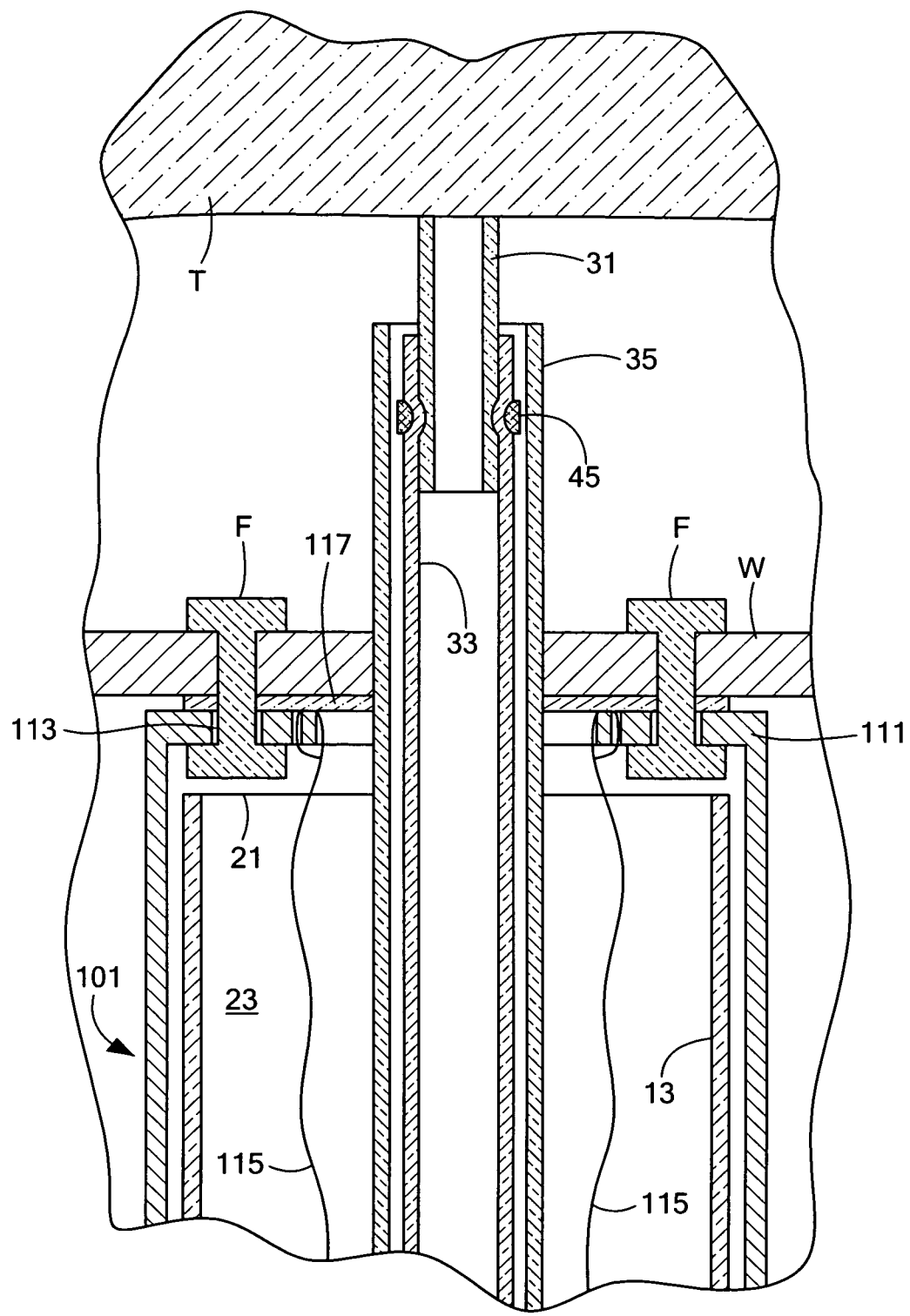

Referring now to FIGS. 5(a) through 5(e), there are shown various views that schematically illustrate one way in which overtube 101 may be used with endoscope 13, injection needle 15 and perforating tool 18 to perform a transluminal injection. (In these views, a transgastric injection is being shown; however, it should be understood that the present invention could alternatively be used to perform a transorgan, transluminal, transesophageal or transintestinal injection.) First, prior to use on a patient, one may load a sterile endoscope 13 distally into a sterile overtube 101 while, at the same time, drawing strings 115 proximally through working channel 23 of endoscope 13. (By holding strings 115 while inserting endoscope 13 into a patient, one may keep endoscope 13 and overtube 101 translationally coupled to one another.) Next, as seen in FIG. 5(a), the distal ends of endoscope 13 and overtube 101 may then be inserted through the mouth of a patient and into the stomach of the patient until distal end 109 of overtube 101 is positioned at a desired location within the stomach of the patient. (Alternatively, one may insert overtube 101 into the patient and then insert endoscope 13 into overtube 101, or one may insert overtube 101 into the patient with a deployment tube positioned therein and then, after insertion of overtube 101 and the deployment tube into the patient, replace the deployment tube with endoscope 13.) Next, as seen in FIG. 5(b), one may then use working channel 23 of endoscope 13 to insert fasteners F across openings 113 and across the stomach wall W of the patient, thereby securing overtube 101 to the stomach wall W. (Alternatively, the fasteners may be coupled to overtube 101 prior to insertion of overtube 101 into the patient, and fastening could occur by pushing overtube 101 against the tissue or by actuating a trigger mechanism to deploy fasteners.) Next, as seen in FIG. 5(c), one may then insert a sterile perforating tool 18 into working channel 23 of endoscope 13 and use perforating tool 18 to perforate film 117 of overtube 101 and stomach wall W. Next, as seen in FIG. 5(d), one may remove perforating tool 18 from endoscope 13 and then insert the distal end of a sterile injection needle 15 (with needle 31 in a fully retracted position) into working channel 23 of endoscope 13 and through the perforations in overtube 101 and stomach wall W until the distal end of injection needle 15 is positioned near a target tissue T in the peritoneal cavity. Next, as seen in FIG. 5(e), one may move needle 31 of injection needle 15 to its extended position and then insert needle 31 into the target tissue T. Materials may then be dispensed into target tissue T through injection needle 15 in the conventional manner. (Alternatively, instead of using injection needle 15 to dispense materials into tissue T, injection needle 15 may be used to aspirate fluids or even to remove tissue.) It should be noted that, because needle 31 may be larger in inner diameter than the needles of conventional injection needles, needle 31 may be better suited for dispensing large volumes of materials, as well as higher viscosity materials and materials including particulate matter, such as radioactive beads, drug delivery matrices, bulking beads and agents, sponges, etc. After the injection of materials into target tissue T is complete, one may move needle 31 back to its fully retracted position and then remove injection needle 15 and endoscope 13 from the patient. Thereafter, fasteners F may be removed, and overtube 101 may be removed from the patient.

It should be understood that, although the above-described method involves a transoral introduction of kit 11 into a patient, a transanal approach may alternatively be used. One factor that may be considered in determining whether to utilize a transoral approach or a transanal approach is the location of the target structure in the patient and, hence, the optimal location for entering the abdominal cavity from the gastrointestinal tract.

Figure 6A:
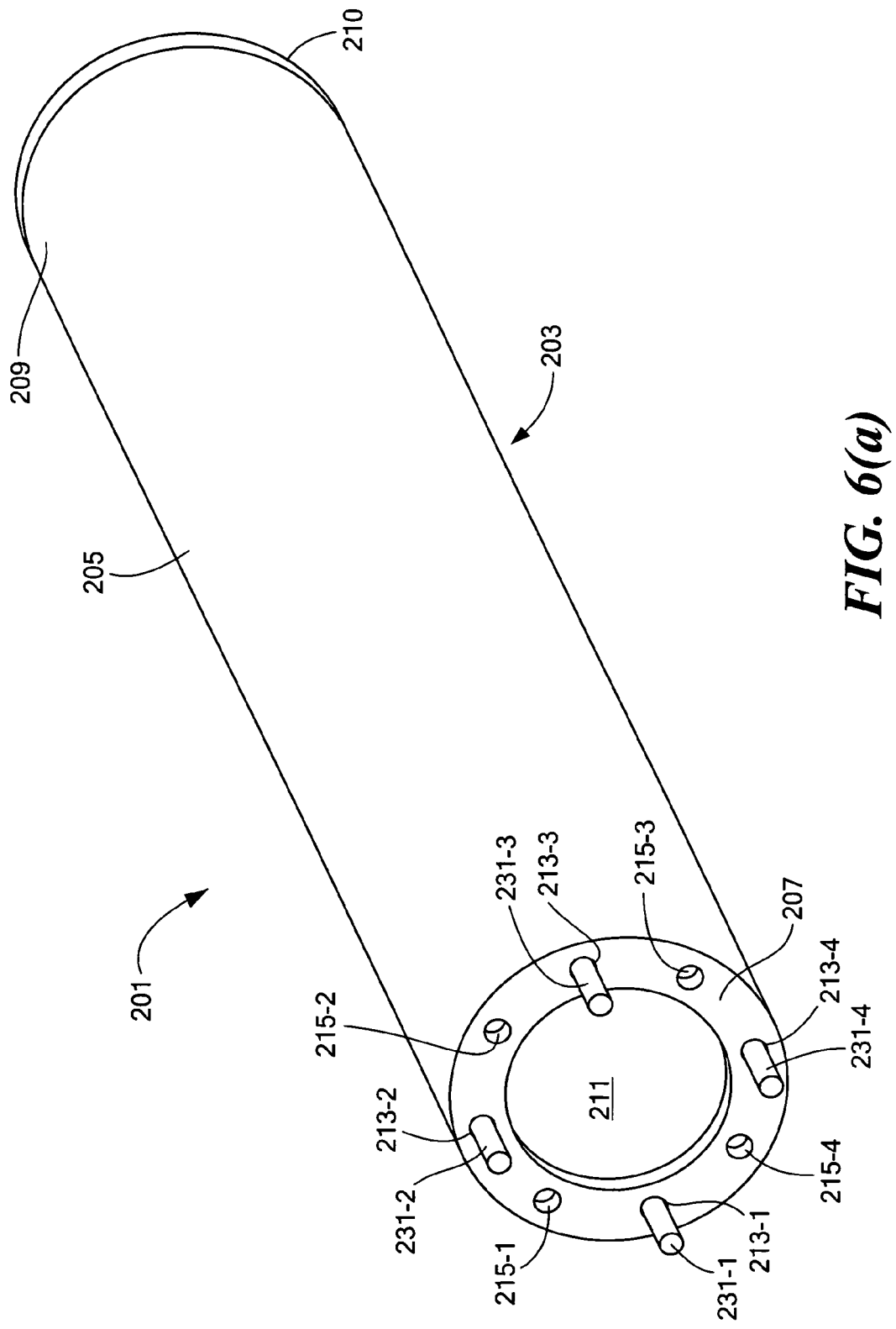
FIGS. 6(a) and 6(b) are proximal perspective and fragmentary longitudinal section views, respectively, of a second alternate overtube for use in the transluminal surgery kit of FIG. 1.
Figure 6B:
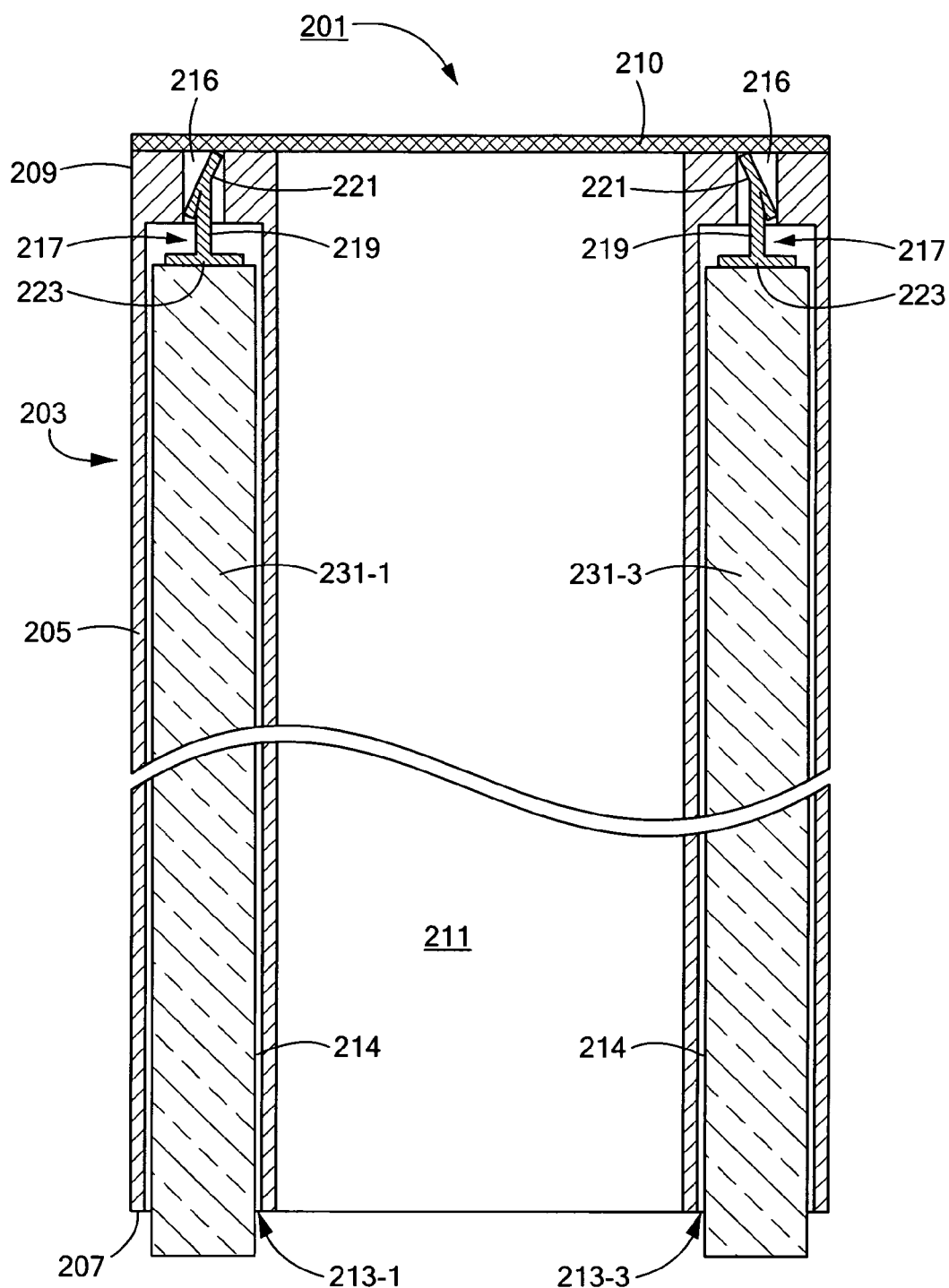

Referring now to FIGS. 6(a) and 6(b), there are shown proximal perspective and fragmentary longitudinal section views, respectively, of a second alternate embodiment of an overtube adapted for use with kit 11, said overtube being represented generally by reference numeral 201.

Overtube 201 may comprise an elongated, tubular member 203. Tubular member 203 may be a unitary structure made of a preferably flexible, biocompatible material, such as a silicone rubber, a thermoplastic elastomer or a similar material. For reasons to be discussed below, tubular member 203 may be constructed to be radially expandable, for example, by being made of an elastic material or by having a corrugated, accordion or folded shape. Tubular member 203 may be shaped to include a side wall 205 terminating in a proximal end 207 and a distal end 209. (Although side wall 205 is shown in the present embodiment as having a cylindrical shape, side wall 205 is not limited to such a shape and may have any geometry, for example, oval.) A thin film 210, which may be optically clear, may sealably cover distal end 209 so that the proper placement of distal end 209 at a desired location within the GI tract may be ensured using visualization means provided in an endoscope positioned within overtube 201. Film 210 may be radially expandable to expand with tubular member 203.

Side wall 205 may be shaped to include a central bore 211. In addition, a first plurality of longitudinal peripheral bores 213-1 through 213-4 and a second plurality of longitudinal peripheral bores 215-1 through 215-4 may be provided in side wall 205. (It should be understood that, although bores 213-1 through 213-4 are shown in FIG. 6(b) as extending the entire length of tubular member 203, i.e., from distal end 209 to proximal end 207, bores 213-1 through 213-4 may instead extend proximally from distal end 209 to some intermediate point that is distal to proximal end 207. For example, bores 213-1 through 213-4 could be reduced in length to the length of distal portions 216. In addition, bores 215-1 through 215-4 need not be straight longitudinal bores extending from proximal end 207 to distal end 209, but rather, may be bent, extending only a portion of the length of member 203 from proximal end 207 to some intermediate point of member 203 that is accessible through wall 205.) Each of bores 213-1 through 213-5 may have a proximal portion 214 of comparatively greater diameter and a distal portion 216 of comparatively lesser diameter. A fastener 217 (such as that disclosed in U.S. Reissue Pat. No. 34,021, which is incorporated herein by reference) suitable for securing tubular member 203 to the patient may be loaded into each of bores 213-1 through 213-4. Fastener 217, which may be made of a biocompatible material (which may also be biodegradable), may be shaped to include a filament 219 having a distal cross-bar 221 disposed at one end thereof and a proximal cross-bar 223 disposed at the opposite end thereof. Distal cross-bar 221 may be disposed within distal portion 216, with distal cross-bar 221 being dimensioned and oriented so as to be retained within distal portion 216 until it is ejected from distal portion 216 in the manner described below. Proximal cross-bar 223 may be dimensioned so that its length exceeds the diameter of distal portion 216, thereby impeding its insertion into distal portion 216.

Pusher rods 231-1 through 231-4 may be slidably disposed in the proximal portion 214 of bores 213-1 through 213-4, respectively. Pusher rods 231-1 through 231-4 may be used to push fasteners 217 distally until distal cross-bars 221 are inserted through film 210 and through the tissue to which overtube 201 is to be anchored. (Because of the length and orientation of proximal cross-bars 223, the proximal ends of fasteners 217 remain within overtube 201.)

One or more of bores 215-1 through 215-4 may be used to dispense a fluid, such as water, from the distal end of overtube 201, for example, to wash debris from a site to which one wishes to secure the distal end of overtube 201. The dispensing of water may be accomplished using, for example, a waterjet or the like inserted distally into each such bore. Alternatively, one or more of bores 215-1 through 215-4 may be used to dispense an antibiotic from the distal end of overtube 201 onto the site to which one wishes to secure the distal end of overtube 201. The application of an antibiotic to the target securing site, which may be done for prophylactic purposes to reduce the likelihood of infection at the site of incision, may be accomplished using a dispensing tube distally inserted into each such bore. Alternatively, one or more of bores 215-1 through 215-4 may be used to apply suction to the site to which one wishes to secure the distal end of overtube 201. This may be done to remove fluid or debris from the site to which one wishes to secure the distal end of overtube 201. Such suction may be applied using a suction tube inserted into each such bore, the proximal end of the suction tube being coupled to a vacuum source or the like. Alternatively, one or more of bores 215-1 through 215-4 may be used for illumination purposes using, for example, an illumination fiber inserted into each such bore. Alternatively, one or more of bores 215-1 through 215-4 may be used to receive ablation fibers to ablate debris at the site to which one wishes to secure the distal end of overtube 201. Alternatively, one or more of bores 215-1 through 215-4 may be used to dispense a sealant for temporary sterility or may be used to apply a temporary adhesive.

As can be appreciated, if film 210 covers the distal ends of bores 215-1 through 215-4, one must puncture film 210 in the areas covering bores 215-1 through 215-4 in order to permit use of bores 215-1 through 215-4. (However, such puncturing may not be necessary if film 210 is optically clear and if the bores are used for illumination and/or ablation purposes.)

Figure 7A:
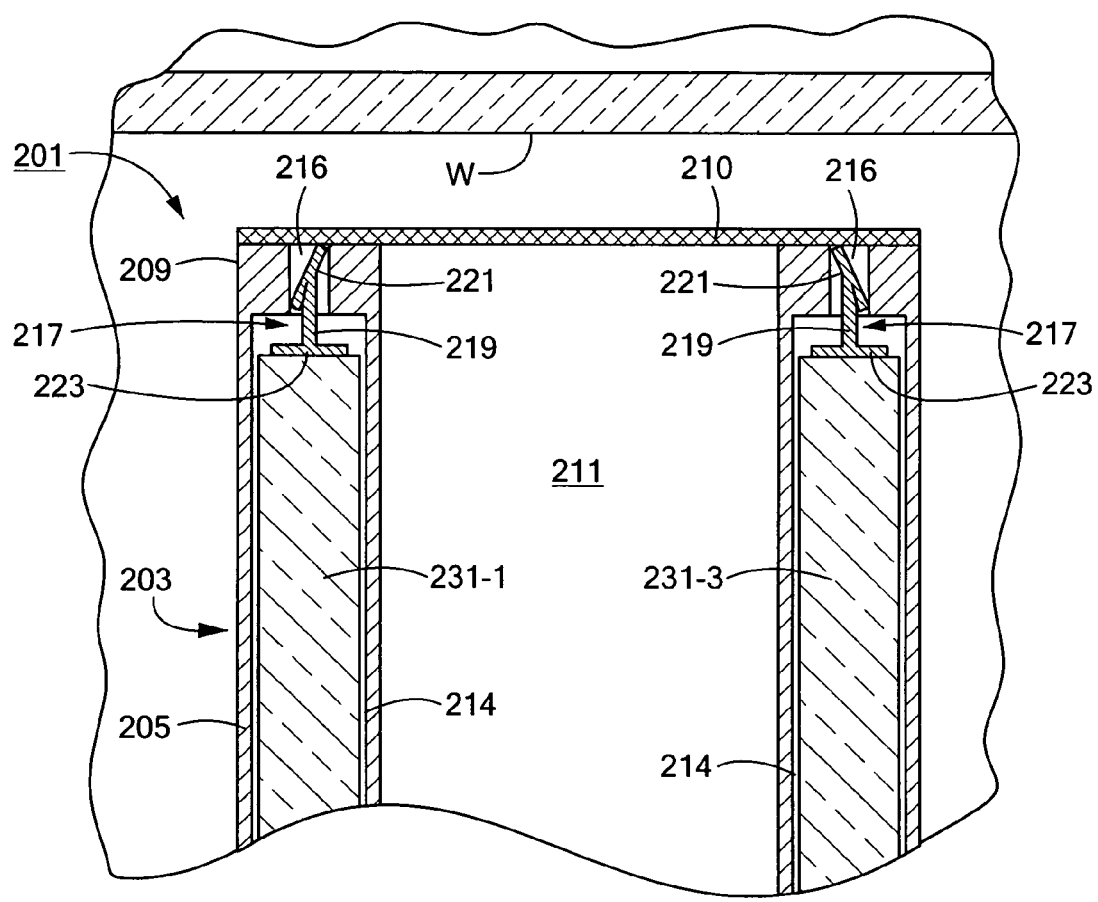
FIGS. 7(a) through 7(h) are fragmentary schematic views, partly in section, illustrating one way in which the overtube of FIGS. 6(a) and 6(b) may be used in accordance with the teachings of the present invention.
Figure 7B:
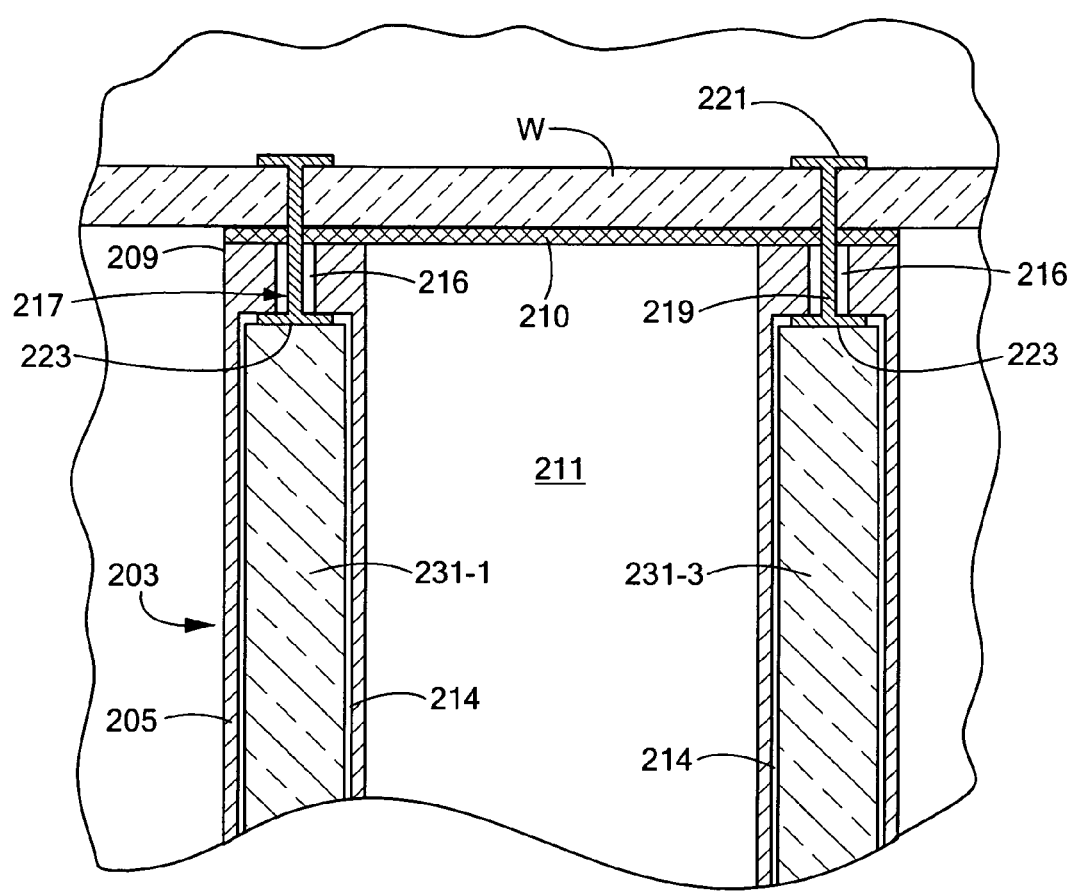
Figure 7C:
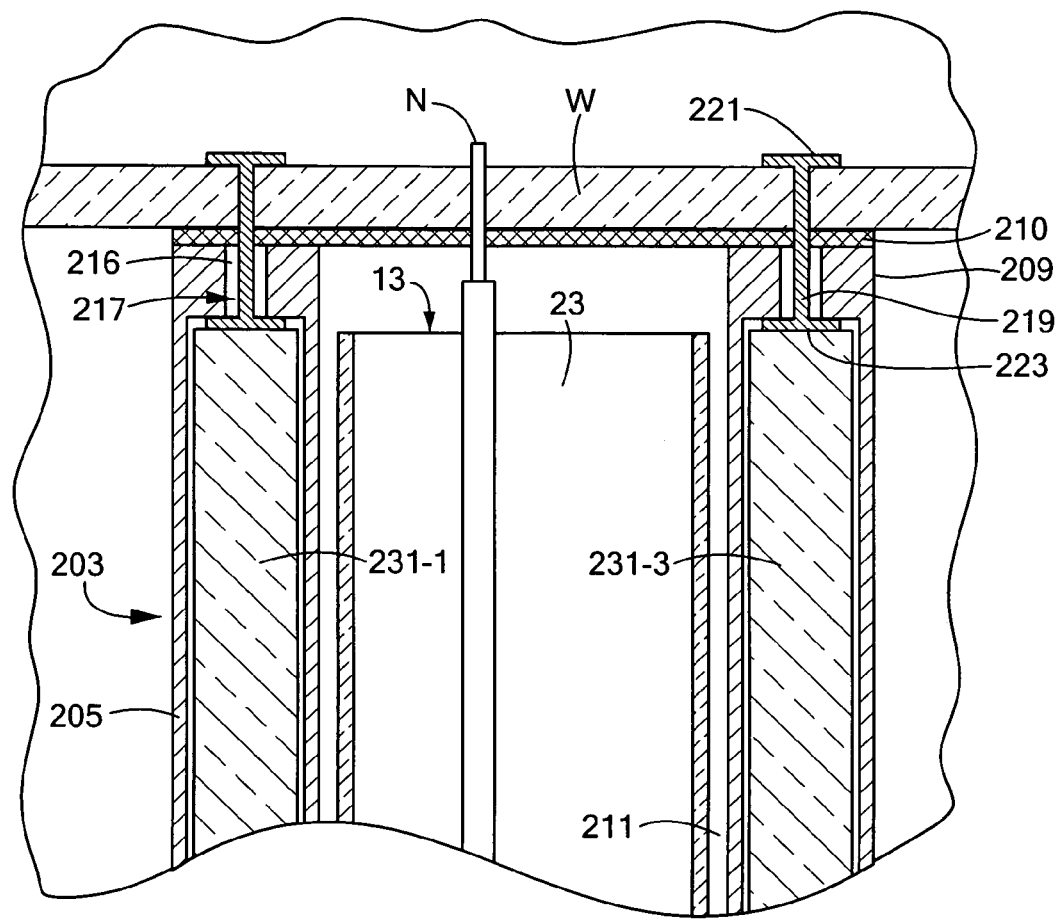
Figure 7D:
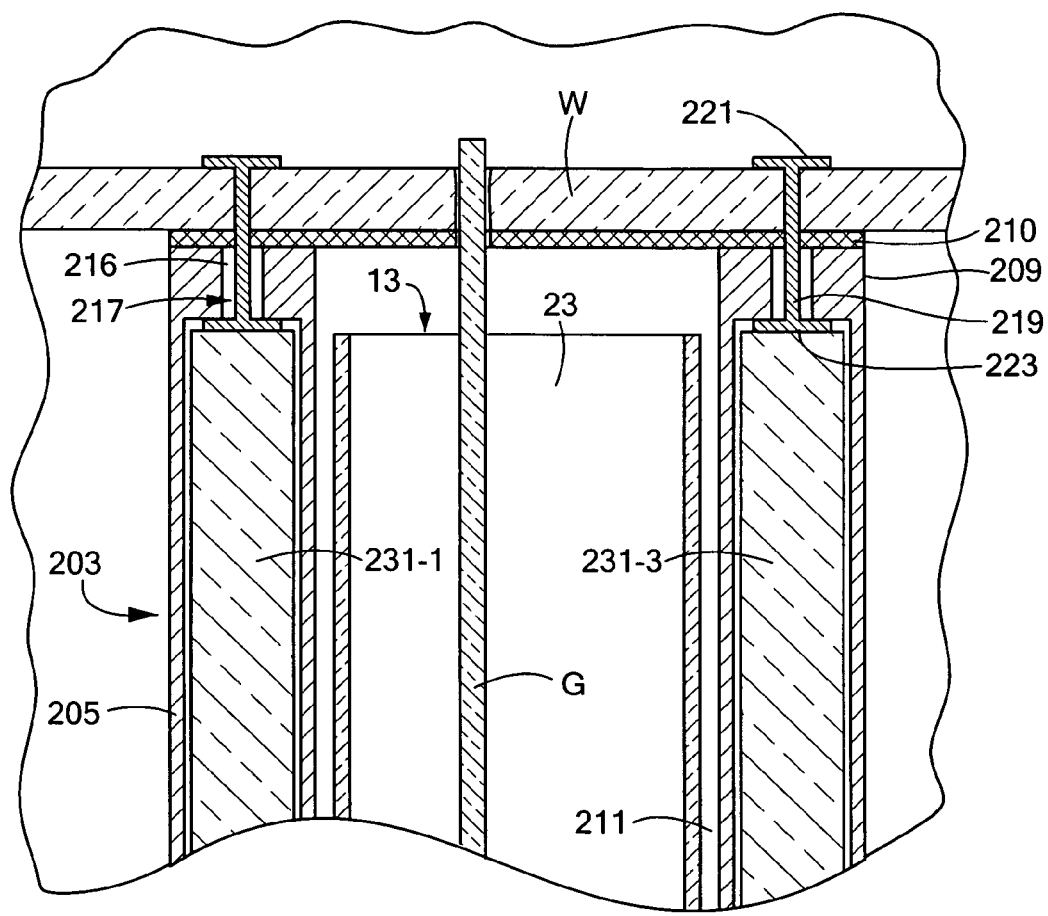
Figure 7E:
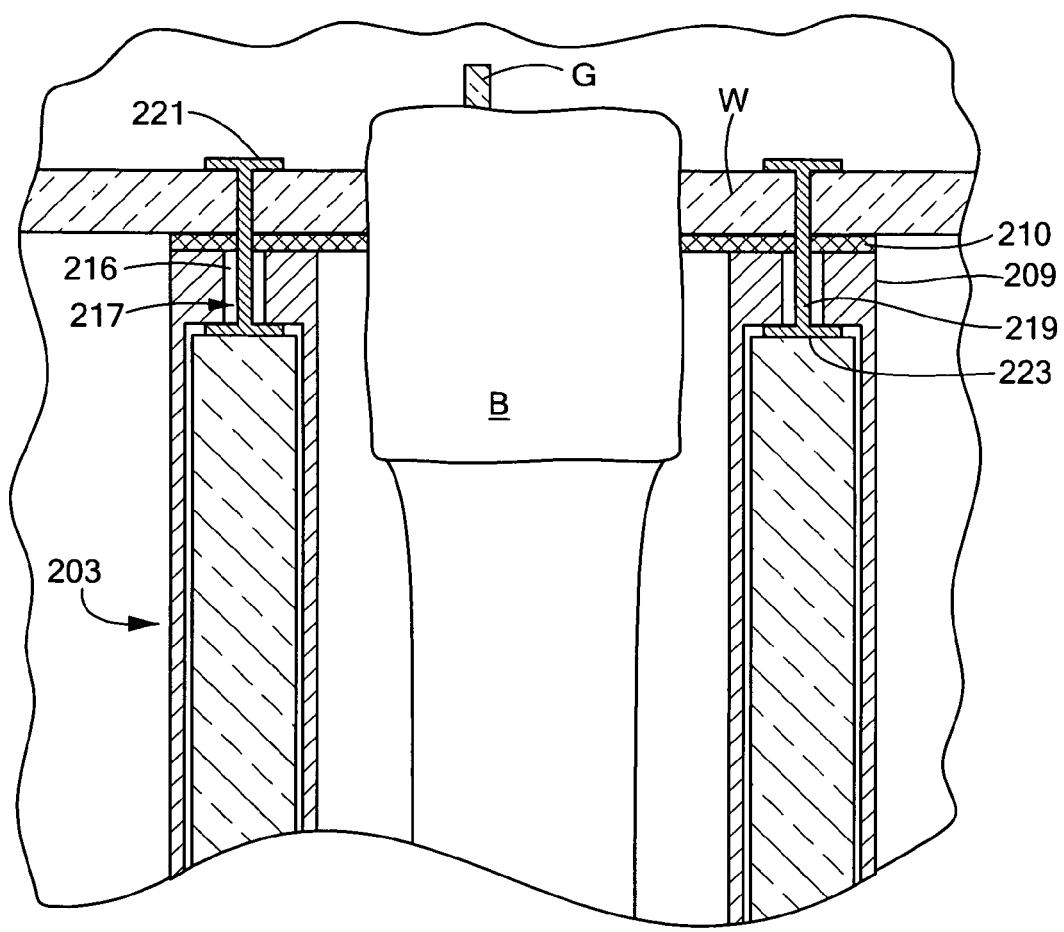
Figure 7F:
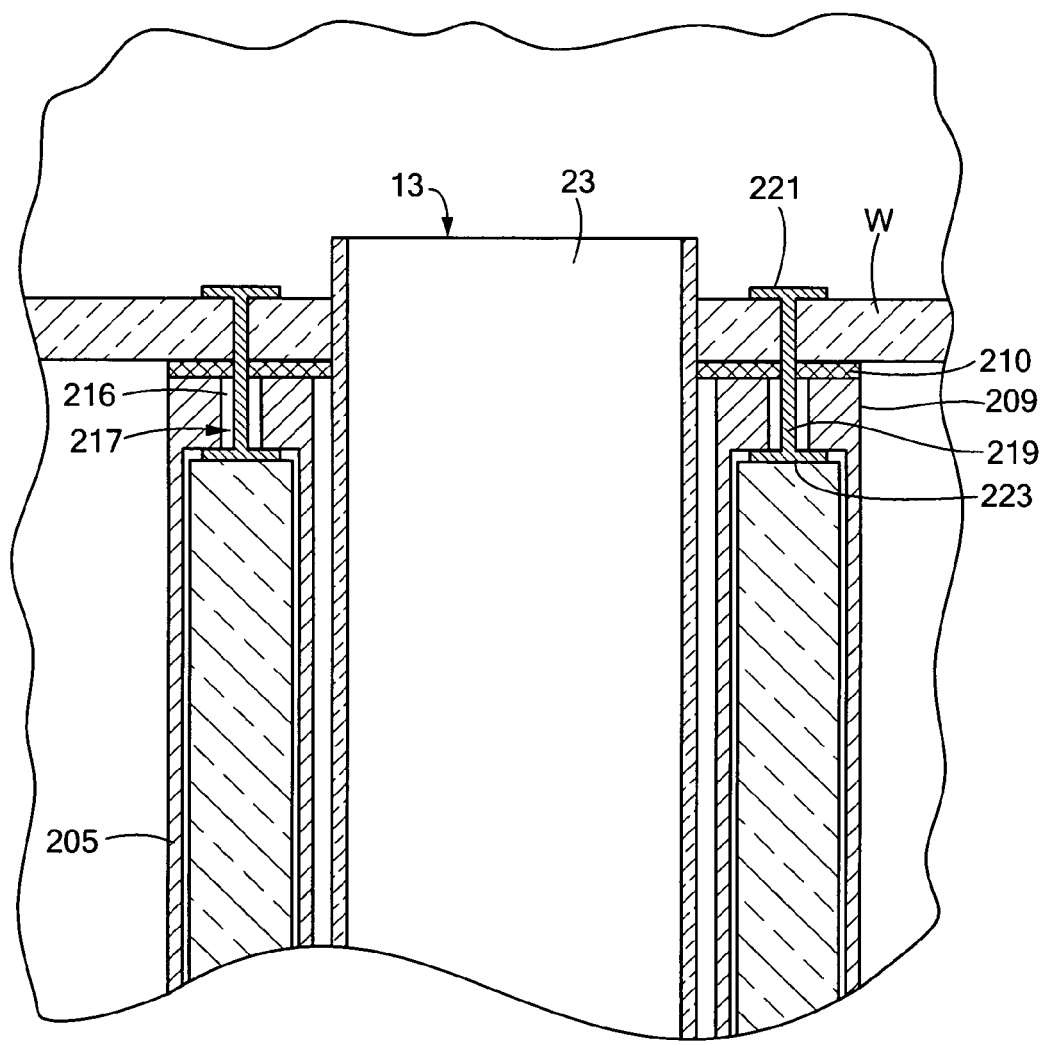
Figure 7G:
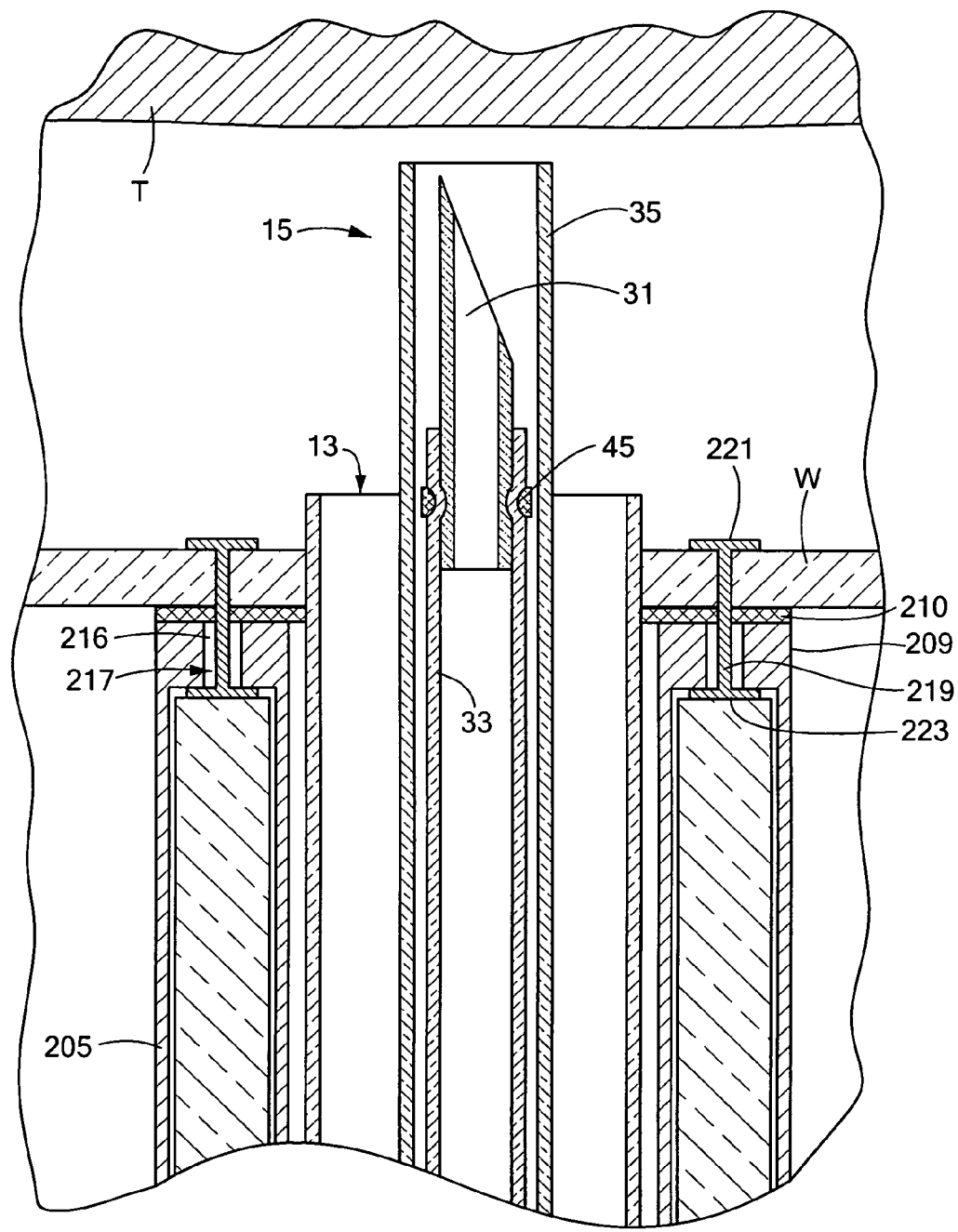
Figure 7H:
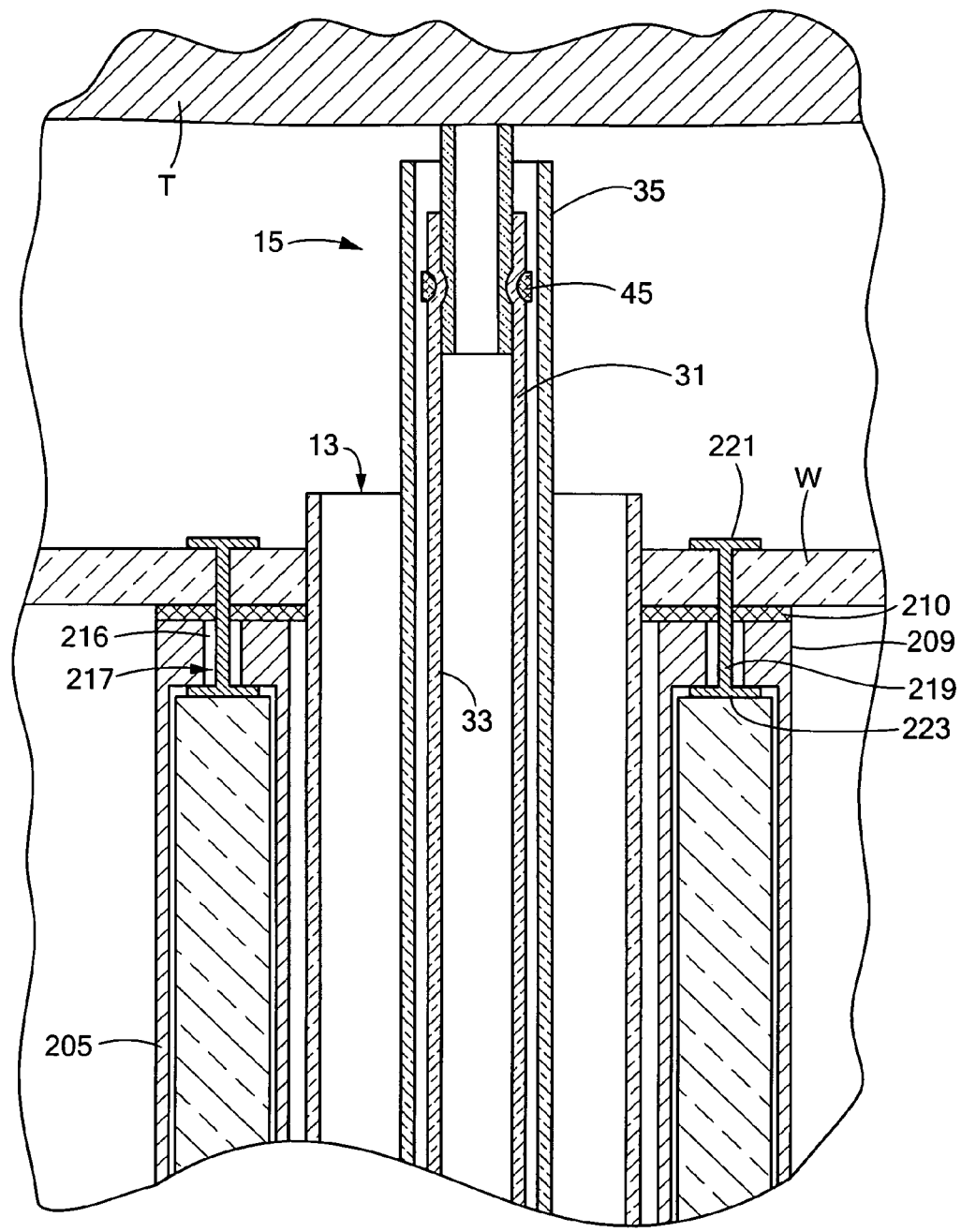

Referring now to FIGS. 7(a) through 7(h), there are shown various views that schematically illustrate one way in which overtube 201 may be used to perform a transluminal injection. (In these views, a transgastric injection is being shown; however, it should be understood that the present invention could alternatively be used to perform a transesophageal, transorgan, transluminal or transintestinal injection.) First, the distal end of overtube 201 may be inserted through the mouth of a patient and into the stomach of the patient until, as seen in FIG. 7(a), the distal end of overtube 201 may be positioned at a desired location within the stomach of the patient. Next, as seen in FIG. 7(b), one may then use pusher rods 231 to insert fasteners 217 through film 210 and across the stomach wall W of the patient, thereby securing overtube 201 to the stomach wall W. (Although fasteners 217 are described herein as being capable of puncturing stomach wall W, one could alternatively use some puncturing device to puncture the stomach wall and then pass fasteners 217 through the punctured stomach wall.) If desired, pusher rods 231 may then be removed from bores 213-1 through 213-4. Next, one may insert a sterile endoscope 13 into overtube 201. A sterile needle knife N or other puncturing device may be loaded into the working channel 23 of endoscope 13 and, as seen in FIG. 7(c), the needle knife N may be used to perforate that portion of film 210 positioned over central bore 211 and may be used to perforate stomach wall W. (Alternatively, instead of inserting needle knife N through endoscope 13, overtube 201 could include a dedicated channel through which needle knife N may be inserted.) Next, as seen in FIG. 7(d), a guide wire G (or guide tube) may be inserted through the perforation in the stomach wall W. Next, a dilating device B, such as a balloon, may be inserted into overtube 201 and across the perforation in the stomach wall W. Next, as seen in FIG. 7(e), dilating device B may be used both to dilate the perforation in the stomach wall W and to expand overtube 201 radially. Next, as seen in FIG. 7(f), endoscope 13 may be inserted through the dilated perforation in the stomach wall W. Next, as seen in FIG. 7(g), one may insert the distal end of a sterile injection needle 15 (with needle 31 in a fully retracted position) into working channel 23 of endoscope 13 and through the perforations in film 210 and stomach wall W until the distal end of injection needle 15 is positioned near a target tissue T in the peritoneal cavity. Next, as seen in FIG. 7(h), one may move needle 31 of injection needle 15 to its extended position and then insert needle 31 into the target tissue T. Materials may then be dispensed into target tissue T through injection needle 15 in the conventional manner. (Alternatively, instead of using injection needle 15 to dispense materials into tissue T, injection needle 15 may be used to aspirate fluids or even to remove tissue.) It should be noted that, because needle 31 may be larger in inner diameter than the needles of conventional injection needles, needle 31 may be better suited for dispensing large volumes of materials, as well as higher viscosity materials and materials including particulate matter, such as radioactive beads, drug delivery matrices, bulking beads and agents, sponges, etc. After the injection of materials into target tissue T is complete, one may move needle 31 back to its fully retracted position and then remove injection needle 15 and endoscope 13 from the patient. Thereafter, fasteners 217 may be removed from stomach wall W, for example, by pulling overtube 201 proximally away from stomach wall W until fasteners 217 break or are withdrawn through stomach wall W. Overtube 201 may then be removed from the patient.

The above procedure is desirable in that it involves forming a relatively small perforation in the stomach wall that is then dilated, as opposed to making a relatively large incision in the stomach wall. As a result, this procedure may promote faster healing of the stomach wall.

It should be understood that, although the above-described method involves a transoral introduction of kit 11 into a patient, a transanal approach or other approaches may alternatively be used. One factor that may be considered in determining whether to utilize a transoral approach, a transanal approach or another lumen is the location of the target structure in the patient and, hence, the optimal location for entering the abdominal cavity from the gastrointestinal tract.

Figure 8:
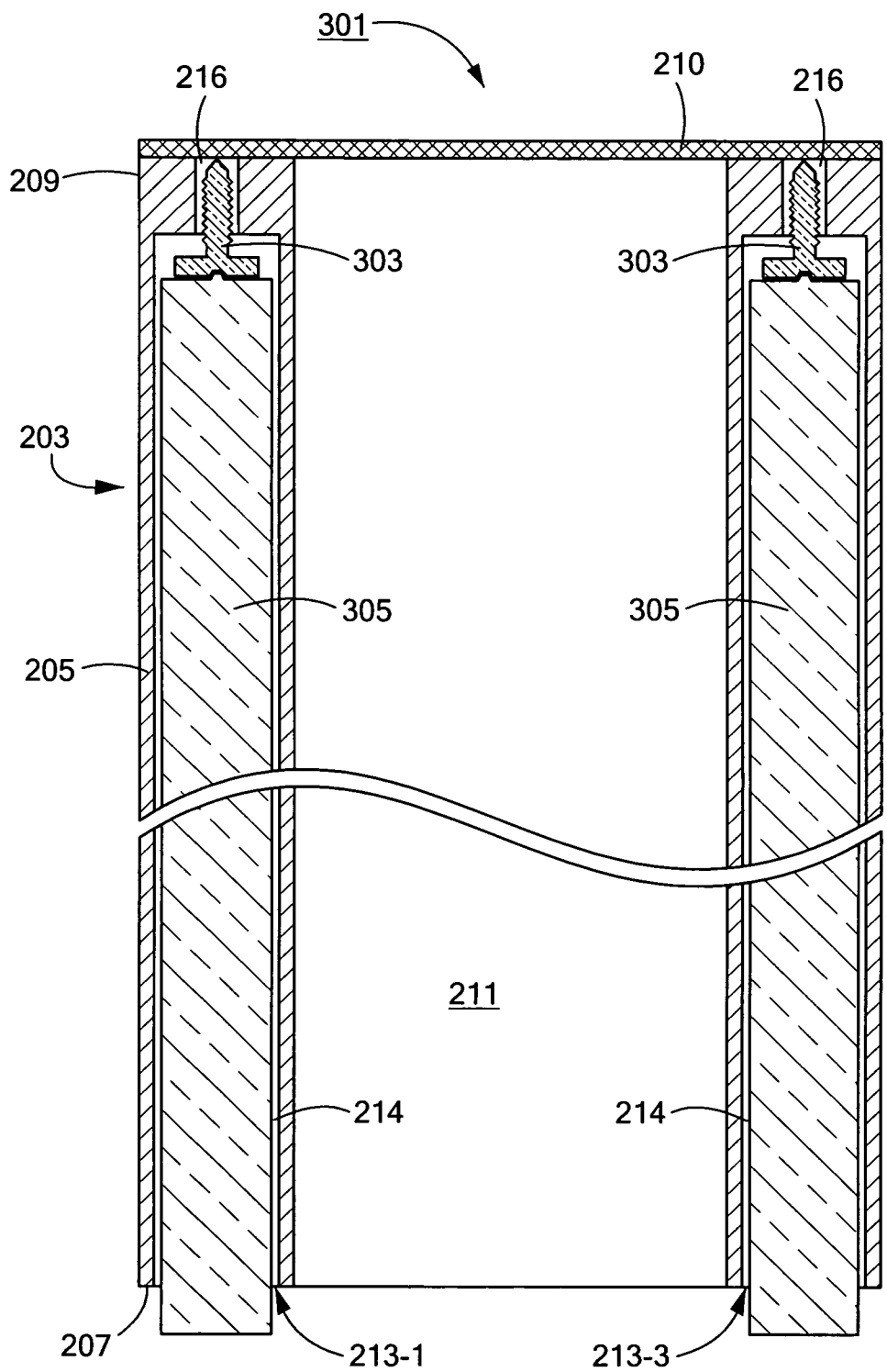
FIG. 8 is a fragmentary longitudinal section view of a third alternate overtube for use in the transluminal surgery kit of FIG. 1.

Referring now to FIG. 8, there is shown a fragmentary longitudinal section view of a third alternate embodiment of an overtube adapted for use with kit 11, said overtube being represented generally by reference numeral 301.

Overtube 301 is similar in most respects to overtube 201, the principal differences between the two overtubes being that, whereas overtube 201 may include corresponding pluralities of fasteners 217 and pusher rods 231, overtube 301 may instead include corresponding pluralities of screws 303 and screwdrivers 305. (Alternatively, screws 303 may be replaced with pointed helical structures, and screwdrivers 305 may be replaced with a rotating rod.) When one wishes to attach tubular member 203 of overtube 301 to the patient, screw 303 may be inserted through bore 213 and seal 210 and then across the GI tract tissue using screwdriver 305. When one wishes to remove overtube 301 from the patient, for example, after a surgical procedure has been performed, screw 303 may be removed from the GI tract tissue using screwdriver 305.

As can readily be appreciated, in any of the embodiments described above, one could replace injection needle 15 with one or more other instruments, such as scissors, suturing devices, graspers, staplers, biopsy needles, forceps, hemostats, cutting wires, or other devices adapted for open surgery or laparoscopic surgery. (Also, injection needle 15 could consist merely of a hypotube having a pointed distal end.) In addition, in any of the embodiments described above, one could replace the sterile endoscope with a sterile access tube or guide tube that may or may not include visualization capabilities. Additionally, in any of the embodiments described above, the puncturing device and the injection needle or the puncturing device and the endoscope may be combined in some fashion (e.g., a pointed stylet extending through the needle, a cap in front of the needle that falls off, a pointed cap on an endosocope, or a device similar to that of U.S. Pat. No. 6,497,686, which is incorporated herein by reference). Moreover, in any of the embodiments described above, one may want the ability to apply suction to the overtube so that, when puncturing occurs, debris is removed from the puncture site, as opposed to being pushed through the puncture site. Furthermore, in any of the embodiments described above, one may wish to have the overtube treated with some agent, e.g., a biocidal agent. Such treatment may be effected by incorporating the agent into a polymer of the overtube, or by applying the agent to a surface of the overtube (such as its distal end surface), or by squirting or otherwise dispensing the agent into the lumen of the overtube.

As can also be appreciated, kit 11 is not limited to the applications described above and may also be suitable for other applications, such as the transcutaneous introduction of vascular and non-vascular catheters, for Swan-ganz catheters which are repositioned and need to stay sterile, for bronchial applications both through the trachea and by transthoracic chest puncture to access the pleural space, for percutaneous substernal approach to the pericardium and the heart, and the like.

The embodiments of the present invention described above are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. An overtube for an access tube, the overtube comprising a tubular member having a central longitudinal axis, a proximal end, a distal end comprising a planar distal surface extending perpendicular to the central longitudinal axis and radially inward toward the central longitudinal axis, and at least one longitudinally-extending bore, the at least one longitudinally-extending bore being adapted to removably receive a distal end of the access tube, the distal end of the tubular member being adapted to secure to a lumen wall within a patient, wherein the distal end of the tubular member comprises a substantially planar cover contacting the planar distal surface and covering a distal end of the longitudinally-extending bore, the cover configured to maintain a sterile environment within the longitudinally-extending bore during insertion of the overtube within the patient.

2. The overtube as claimed in claim 1 wherein the distal end of the tubular member is shaped to include a flange having at least one opening through which a fastening element may be inserted to fix the tubular member to the lumen wall within the patient.

3. The overtube as claimed in claim 2 wherein the flange extends in a radially inward direction.

4. The overtube as claimed in claim 3 wherein a plurality of tabs extend radially inward from the flange.

5. The overtube as claimed in claim 1 wherein the tubular member comprises a proximal portion and a distal portion, the proximal portion being tubular and comprising a distal end and a longitudinal bore, the distal portion covering the distal end of the proximal portion and extending radially outwardly therefrom to define an external flange, a plurality of transverse openings being provided on the distal portion at positions located radially outwardly of the proximal portion.

6. The overtube as claimed in claim 1 wherein the cover is a film, the distal end of the tubular member being generally annular and being shaped to include a plurality of tabs extending into a central opening, the film covering the central opening and contacting the plurality of tabs.

7. The overtube as claimed in claim 6 further comprising a string secured to a tab, the string extending proximally through the longitudinally-extending bore.

8. The overtube as claimed in claim 7 further comprising a plurality of strings, each of the strings being secured to a different tab and extending proximally through the longitudinally-extending bore.

9. The overtube as claimed in claim 1 further comprising a fastener for securing the tubular member to the lumen wall within the patient.

10. An overtube for an access tube, the overtube comprising a tubular member having a central longitudinal axis, a proximal end, a distal end comprising a distal surface extending perpendicular to the central longitudinal axis, the distal surface having a plurality of openings, and at least one longitudinally-extending bore defining a central opening, the at least one longitudinally-extending bore being adapted to removably receive a distal end of the access tube, the distal end of the tubular member being adapted to secure to a lumen wall within a patient, wherein the distal end of the tubular member comprises a cover extending across and covering a distal end of the central opening and the plurality of openings in the distal surface, and the cover is configured to maintain a sterile environment within the longitudinally-extending bore during insertion of the overtube within the patient.

11. The overtube as claimed in claim 10 wherein the cover extends perpendicular to the central longitudinal axis of the tubular member.

12. The overtube as claimed in claim 10, further including a flange, the flange having the distal surface and the plurality of openings.

13. The overtube as claimed in claim 12, further including a plurality of tabs protruding radially inwardly from the flange.

14. The overtube as claimed in claim 10, wherein the cover includes a film.

15. The overtube as claimed in claim 10, wherein the plurality of openings receive a plurality of fasteners configured to secure the tubular member to the lumen wall within the patient.

16. The overtube as claimed in claim 10, further including a plurality of strings coupled to the distal surface.

* * * * *